United States Patent
Barrett et al.

(10) Patent No.: US 9,663,826 B2
(45) Date of Patent: May 30, 2017

(54) SYSTEM AND METHOD OF GENOMIC PROFILING

(71) Applicant: THE TRANSLATIONAL GENOMICS RESEARCH INSTITUTE, Phoenix, AZ (US)

(72) Inventors: Michael T. Barrett, Scottsdale, AZ (US); Elizabeth Lenkiewicz, Scottsdale, AZ (US); Tara Holley, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 280 days.

(21) Appl. No.: 14/378,650

(22) PCT Filed: Feb. 15, 2013

(86) PCT No.: PCT/US2013/026532
§ 371 (c)(1),
(2) Date: Aug. 13, 2014

(87) PCT Pub. No.: WO2013/123463
PCT Pub. Date: Aug. 22, 2013

(65) Prior Publication Data
US 2015/0031556 A1    Jan. 29, 2015

Related U.S. Application Data

(60) Provisional application No. 61/599,317, filed on Feb. 15, 2012.

(51) Int. Cl.
*C12Q 1/68* (2006.01)

(52) U.S. Cl.
CPC ......... *C12Q 1/6886* (2013.01); *C12Q 1/6806* (2013.01); *C12Q 1/6809* (2013.01); *C12Q 1/6827* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2004/0175717 A1 | 9/2004 | Van Zyl |
| 2009/0176271 A1 | 7/2009 | Durack et al. |
| 2010/0162419 A1 | 6/2010 | Hlatky |
| 2010/0167953 A1 | 7/2010 | Ballif et al. |
| 2011/0229917 A1 | 9/2011 | Krizman et al. |
| 2011/0230358 A1 | 9/2011 | Rava |

FOREIGN PATENT DOCUMENTS

WO    2009/055366 A1    4/2009

OTHER PUBLICATIONS

Hendy-Ibbs et al (1987) "Flow cytometric quantitation of DNA and c-myc oncoprotein in archival biopsies of uterine cervix neoplasia" British Journal of Cancer 55(3):275-82.*
Wagle et al (2012) "High-throughput detection of actionable genomic alterations in clinical tumor samples by targeted, massively parallel sequencing" Cancer Discovery 2(1):82-93.*
BD Influx™ Cell Sorter User's Guide (2011) bdbiosciences.com, 23-11543-00 Rev. 01.*
Hirsch et al. (2011) "Isothermal whole genome amplification of FFPE samples to detect copy number changes in the progression from colonic adenoma to carcinoma" Cancer Research 71(8 Suppl):Abstract 3073.*
Amsterdam et al. (1972) "Structural and Functional Characterization of Isolated Pancreatic Exocrine Cells" Proceedings of the National Academy of Sciences 69(10):3028-3032.*
Agilent Technologies (2009) "Agilent Oligonucleotide Array-Based CGH for Genomic DNA Analysis" Version 6.2 Protocol, part No. G4410-90010.*
Vergani et al., "Identification of MET and SRC Activation in Melanoma Cell Lines Showing Primary Resistance to PLX4032", Neoplasia, 13(12):1132-1142 (2011).
Ruiz et al., "Advancing a clinically relevant perspective of the clonal nature of cancer", Proceedings of the National Academy of Sciences, 108(29):12054-12059 (Jul. 19, 2011).
Navin et al., "Inferring tumor progression from genomic heterogeneity", Genome Research, 20(1):68-80 (Jan. 2010).
Belien et al., "Gross genomic damage measured by DNA image cytometry independently predicts gastric cancer patient survival", British Journal of Cancer, 101(6):1011-1018 (Sep. 15, 2009).
Banez et al., "False aneuploidy in benign tumors with a high lymphocyte content: A study of Warthin's tumor and benign thymoma", Human Pathology, 23(11):1244-1251 (Nov. 1992).
Adiga et al., "Androgen receptor expression and DNA content of paraffin-embedded archival human prostate tumors", Cytometry, 50(1):25-30 (2002).
Brandal et al., "Molecular cytogenetic characterization of desmoid tumors", Cancer Genetics and Cytogenetics, 146 (1):1-7 (2003).
Hedley et al., "Method for Analysis of Cellular DNA Content of Paraffin-embedded Pathological Material Using Flow Cytometry", The Journal of Histochemistry and Cytochemistry, 31(11):1333-1335 (1983).
Shono et al., "Relationship between flow cytometric DNA ploidy and nuclear grade with endocrine dysfunction in adrenal cortical adenomas", Urology, 56(2):337-341 (2000).
Holley et al., "Deep Clonal Profiling of Formalin Fixed Paraffin Embedded Clinical Samples", PLOS ONE, 7(11): e50586 (Nov. 2012).
International Search Report and Written Opinion of the International Searching Authority for corresponding application No. PCT/US2013/026532 dated Jul. 11, 2013.
Extended European Search Report for corresponding EP application No. 13749864.8 dated Sep. 10, 2015.

* cited by examiner

*Primary Examiner* — Karen S Weiler
(74) *Attorney, Agent, or Firm* — Rodney J. Fuller; Booth Udall Fuller, PLC

(57) ABSTRACT

The present invention relates to a system and method of genomic profiling and is particularly useful in genomic differentiation of heterogeneous and polyclonal neoplastic cell populations, preferably of flow sorted formalin fixed paraffin embedded samples. The present invention includes methods of improving resolution for identifying aberration in variable carcinoma genomes and/or heterogeneous cell populations. The present invention also includes kits configured to improve genomic resolution and the ability to identify genomic aberration in variable and/or heterogeneous cell populations.

18 Claims, 39 Drawing Sheets
(6 of 39 Drawing Sheet(s) Filed in Color)

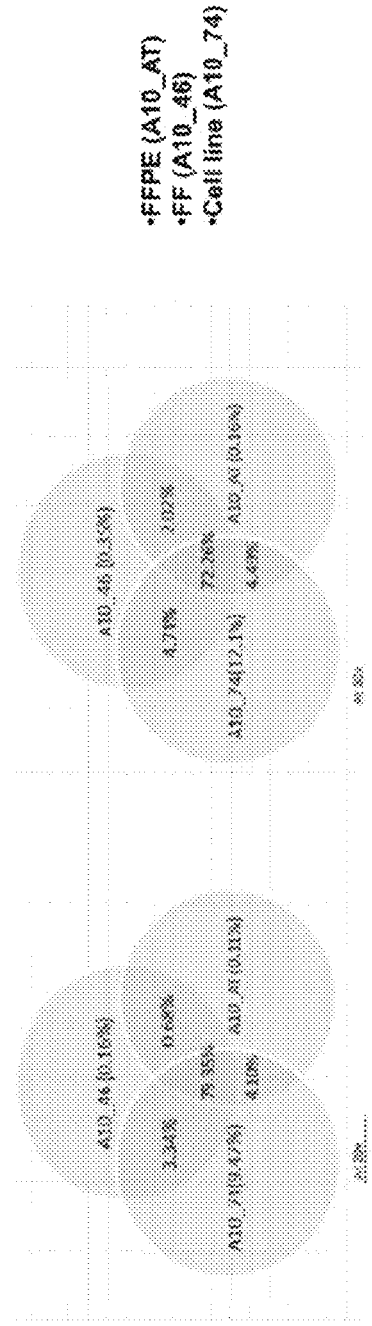
Figure 6

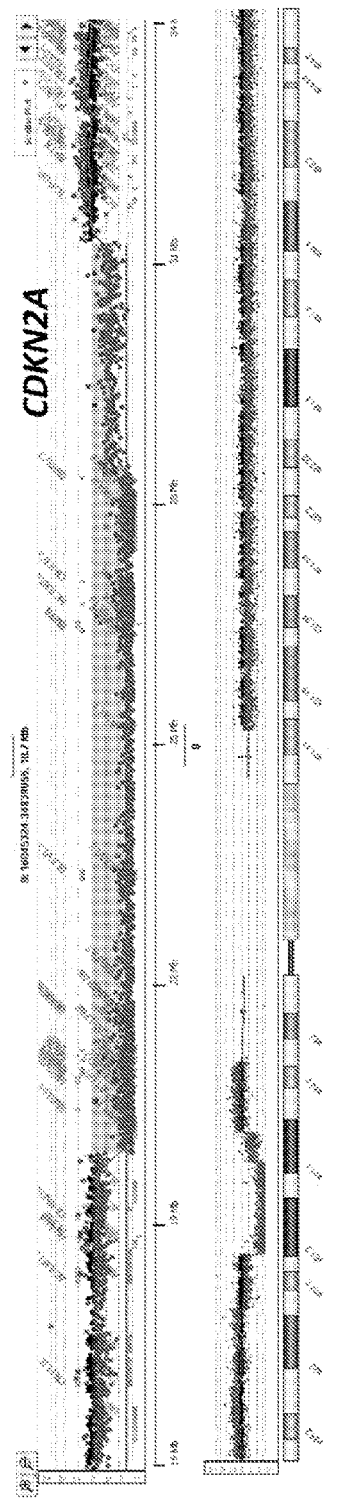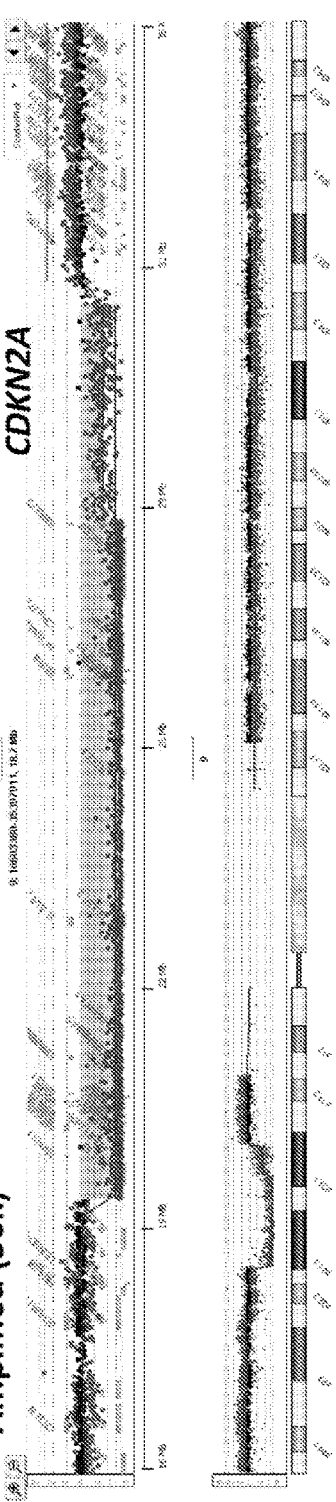
Figure 8

Figure 10

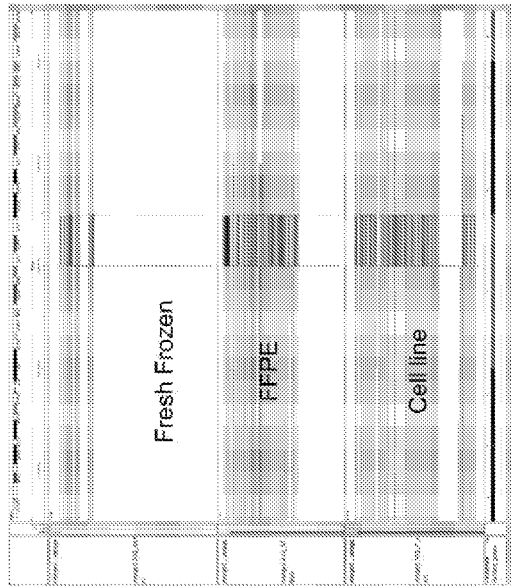
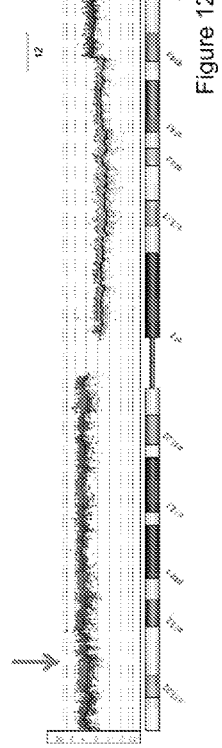
Figure 12

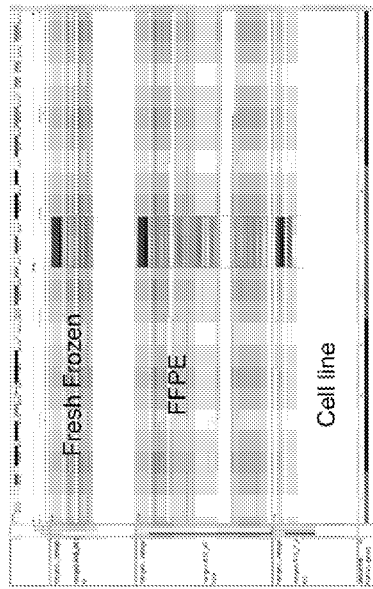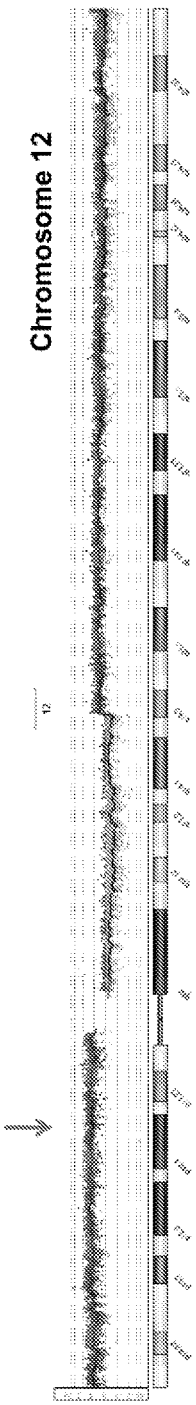
Figure 13

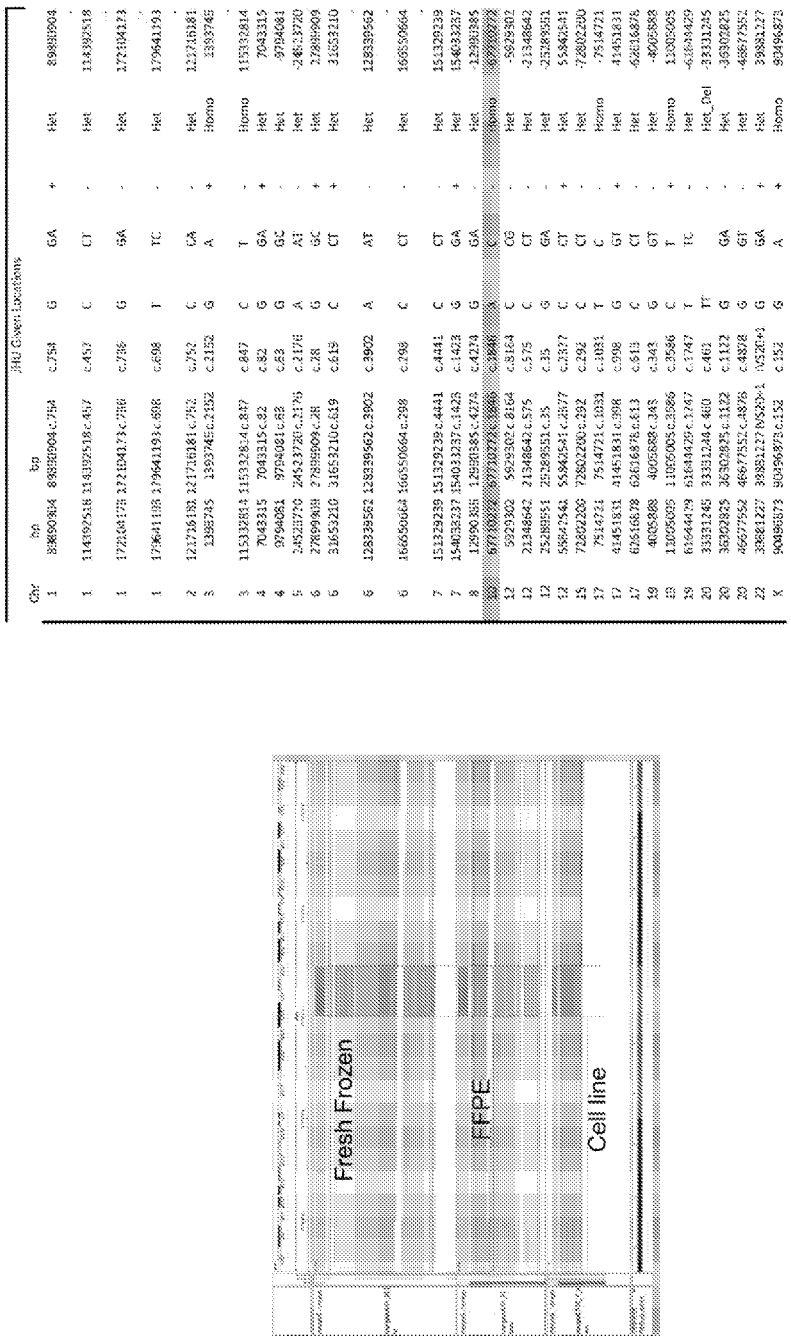
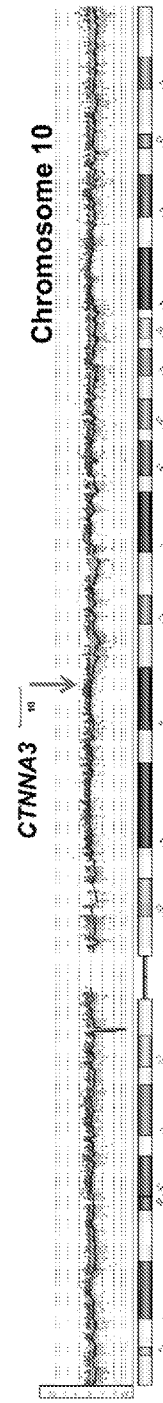
Figure 14

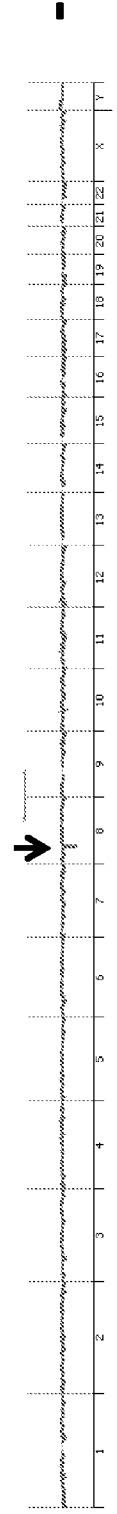
Figure 32

SYSTEM AND METHOD OF GENOMIC PROFILING

CROSS-REFERENCE TO RELATED APPLICATION

This application is the U.S. National Stage of International Application No. PCT/US2013/026532 filed Feb. 15, 2013, which claims the benefit of U.S. Provisional Application No. 61/599,317, filed Feb. 15, 2012, the contents of each of which are incorporated herein by reference in their entireties for all purposes.

STATEMENT REGARDING FEDERALLY SPONSORED RESEARCH

This invention was made with government support under CA137687 awarded by the National Institutes of Health. The government has certain rights in this invention.

FIELD OF THE INVENTION

This invention relates to a system and method of genomic profiling. The system and method are effective at genomic profiling of heterogeneous and polyclonal neoplastic cell populations. In particular embodiments, the system and methods more specifically relate to deep genomic profiling of flow sorted formalin fixed paraffin embedded clinical samples.

BACKGROUND OF THE INVENTION

Clinical tissue samples are formalin fixed and paraffin embedded (FFPE) to preserve the samples for archival purposes. Such FFPE tissue samples include samples from tumors, which often include heavy admixtures of normal cells and tumor cells. FFPE tissue samples are a vast resource of clinically annotated samples with patient follow-up data including diagnostic and therapeutic outcomes. As such, these samples represent highly desirable and informative materials for the application of high definition genomics that could improve patient management and provide a molecular basis for the selection of personalized therapeutics. The availability of well annotated archived samples represents a highly favorable resource to study the basis of therapeutic responses and the clinical history of human cancers. Fragment size of DNA template, however, is very low for extracted FFPE material.

The recent development of whole exome and whole genome technologies provides an unparalleled opportunity for advances in improved treatment and diagnosis for patients with cancer. One major limitation to the use of routinely prepared FFPE tissue samples to date is the highly variable quality of the DNA extracted from samples of interest. In addition, high-resolution molecular analyses of biomaterials from human specimens are highly dependent on the cellular composition of the specimens. For example, a high degree of surrounding normal cells in a tumor tissue can make it difficult to isolate a sufficient number of neoplastic cells for high definition analysis of cancer genomes.

The poor quality of DNA from FFPE samples and the highly heterogeneous tumor content of tumor samples are barriers to effectively utilizing the huge number of FFPE samples available for study. The use of FFPE is currently very limited for next-generation sequencing because of sample degradation and heavy admixtures of normal and tumor cells. Current efforts in next-generation sequencing are targeting high number reads (e.g., >100×) to overcome tissue heterogeneity. Increasing read number, however, only exacerbates errors associated with poor quality samples.

Recent studies have described various methods to interrogate FFPE samples with advanced array and sequencing technologies. These typically select samples exceeding a threshold for tumor cell content based on histological methods, such as, evaluation of H&E stained slides, use of macrodissection, or laser capture approaches prior to analysis. Once selected, samples are typically extracted in bulk using various protocols consisting of dewaxing, removal of cross links, and subsequent DNA extraction and purification. Array and sequencing analyses of these samples typically require relatively large amounts of starting material to achieve appropriate signal to noise levels. However, many samples, notably tumors arising in solid tissues, exhibit high degrees of tissue heterogeneity with varied admixtures of reactive stroma, inflammatory cells and necrosis in immediate contact with tumor cells.

Furthermore, it is well established that biopsies frequently contain multiple clonal populations of neoplastic cells that cannot be distinguished on the basis of morphology alone. Consequently, histology-based methods cannot readily distinguish whether aberrations in a tumor are present in a single cancer genome or if they are distributed in multiple clonal populations. Thus, current approaches for the analyses of cancer genomes using FFPE samples are limited and lacking in their ability to determine the clinical context of each patient's tumor.

A similar problem is seen in clinical diagnostic settings. While the issue of degraded DNA due to tissue fixing is not present, the difficulty in providing high-resolution genetic profiling still exists. One approach is passage of tumor biopsies in tissue culture or in xenografts. These methods apply selective pressures on the complex mixtures of cells and clones present in a patient sample, are time-consuming, labor intensive, and are not amenable to rapid deployment in most clinical settings. Consequently, the number of xenografts successfully grown varies from site-to-site, and the biological complexity and clinical context of the patient sample may not be reflected in the final processed sample.

Flow cytometry-based cell sorters can select, objectively measure, and sort individual particles such as cells or nuclei using desired features objectively defined by fluorescent and light scattering parameters in a flow stream. Recent advances in this technology provide high throughput flow rates and the detection of relatively rare events in dilute admixed samples, enabling the application of flow cytometry to in vivo high definition analyses of human cancers. Different reports have shown that tumor cells can be efficiently sorted from FFPE samples using DNA content based assays. Sorted FFPE samples have been used for PCR based assays and SNP arrays. However, these approaches typically have limited resolution in the number of genes and loci interrogated. Furthermore, the use of SNP arrays requires the use of reduced complexity samples.

The combination of flow sorting and genomic analyses has been recently used for the enrichment of pancreas carcinoma cells and to study the clonal composition of primary breast tumors. These studies, however, relied on extensive bioinformatic analyses, platform-specific sample preparations, or relatively large amounts of input material to achieve an acceptable signal-to-noise ratio in their genome analyses. Further, the methods of such studies become even more unfeasible if applied to FFPE samples, where the added problem of DNA degradation is present. A need exists for an improved system and method of identifying aberrations in cell and tissue samples, especially in complex, variable carcinoma genomes derived from FFPE. One object of the present invention is to provide a system and method with improved resolution to facilitate the differentiation and identification of these aberrations. See, e.g., Ibrahim, S F, et al. (2007), "Flow cytometry and cell sorting." *Adv Biochem Eng Biotechnol* 106:19-39; Navin N, et al. (2010), "Inferring tumor progression from genomic heterogeneity." *Genome Res* 20:68-80; and, Boyd Z S, et al. (2009), "A tumor sorting protocol that enables enrichment of pancreatic adenocarcinoma cells and facilitation of genetic analyses." *J Mol Diagn* 11:290-297, which are each herein incorporated by reference for all purposes.

BRIEF SUMMARY OF THE INVENTION

The present invention provides methods of profiling genomes. In a particular embodiment, the method is used to identify aberrations in a variable cancer cell genome sample. The method comprises the steps of: obtaining a cancerous tumor sample comprising normal and/or abnormal cells; creating a suspension of de-agglomerated nuclei of the cells suitable for flow sorting; sorting the nuclei into a plurality of fractions (e.g., 2, 3, 4, or 5, etc.) based at least on a quantification of genetic material in the nuclei; extracting the genetic material from at least a portion of the sorted nuclei (e.g., at least about 10,000, 25,000, or 50,000); differentially labeling the extracted genetic material and a reference sample; hybridizing the labeled extracted genetic material and reference sample on a feature comparative genomic hybridization array; and comparing the labeled extracted genetic material with the labeled reference sample to determine aberrations unique to the labeled extracted genetic material.

According to embodiments, the aberrations are detected using an aberration detection algorithm as shown in the examples below.

In certain embodiments, the method further comprises the step of inferring an evolution of the tumor based on a comparison between aberrations in the genetic material from the plurality of fractions and/or treatment history of the patient. Still further, the method may further include the step of: sequencing the extracted genetic material by preparing a fragmented library, comprising a whole genome library and/or an exome library from the extracted genetic material; amplifying the fragmented library by generating a plurality of paired-end clusters from a plurality of fragments from the fragmented library; and, determining the sequence of the plurality of fragments through parallel sequencing. The sample can be from any cancerous or neoplastic tumor, preferably carcinoma. The sample may be, for example, from breast cancer, large intestinal cancer, lung cancer, small lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, vaginal carcinoma, Hodgkin's disease, non-Hodgkin's lymphoma, esophageal cancer, small intestine cancer, endocrine cancer, thyroid cancer, parathyroid cancer, adrenal cancer, chronic or acute leukemia, soft tissue tumor, urethral cancer, penile cancer, prostate cancer, lymphocytic lymphoma, bladder carcinoma, kidney cancer, ureter cancer, renal carcinoma, renal pelvic carcinoma, CNS tumor, primary CNS lymphoma, bone marrow tumor, brain stem nerve gliomas, pituitary adenoma, testicular cancer, oral cancer, pharyngeal cancer and uveal melanoma. More specifically, for example, prostate adenocarcinoma, a pancreatic adenocarcinoma, a breast carcinoma, a bladder carcinoma, a glioblastoma, an ovarian carcinoma, or a melanoma.

The invention is also directed to a method of identifying aberrations in a variable cancer cell genome derived from a FFPE tissue sample. In this particular embodiment, the method typically includes the steps of: dewaxing a FFPE tissue sample; rehydrating the tissue sample; treating the tissue sample to obtain a suspension of de-agglomerated nuclei suitable for flow sorting (e.g., processing the tissue with EDTA, collagenase, and hyaluronidase); sorting the nuclei into a plurality of fractions based at least on a quantification of genetic material in the nuclei; profiling the ploidy and cell cycle fractions of the nuclei; extracting the genetic material from at least a portion of the sorted nuclei; amplifying the genetic material through single primer isothermal amplification; and, digesting the genetic material to substantial uniformity with an endonuclease, preferably with DNAse 1. This embodiment may further include the steps of differentially labeling the digested genetic material and a reference sample; hybridizing the labeled digested genetic material and reference sample on a feature comparative genomic hybridization array; and/or comparing, with an aberration detection algorithm, the labeled digested genetic material with the labeled reference sample to infer aberrations unique to the labeled digested genetic material.

Additional optional steps may include: preparing from the flow sorted genetic material a fragmented library comprising a whole genome library or an exome library from the extracted genetic material; amplifying the fragmented library by generating a plurality of paired-end clusters from a plurality of fragments from the fragmented library; and, determining the sequence of the plurality of fragments through parallel sequencing.

Prior to sorting the nuclei, the method may also include the step of staining the nuclei with, for example, 4',6-diamidino-2-phenylindole.

A copy number aberrant genomic interval in the extracted genetic material is considered similar to an interval in another sample, for example, when an overlap exceeds about 0.3, 0.4, or 0.5, wherein the overlap of two aberration intervals comprises the genomic length of their intersection divided by the genomic length of their union.

The invention is also directed to a master kit configured to identify aberrations in variable cancer cell genomes derived from a formalin fixed paraffin embedded (FFPE) tissue sample. The master kit may comprise a FFPE tissue preparation solutions, a DNA extraction kit, a single primer isothermal amplification kit, and an endonuclease. For example, in a specific embodiment, the master kit may comprise a microcentrifuge tube configured to receive a sectioned piece of a cancerous FFPE tissue sample; a solvent to remove paraffin from the FFPE tissue sample; an alcohol to rehydrate the tissue sample; a coordination compound to facilitate the removal of protein cross-links present in the tissue sample; a phosphate-buffered saline solution; an enzymatic cocktail comprising, for example, collagenase, hyaluronidase, and a buffer, to free nuclei from the tissue; a fetal bovine serum buffer; an agitator for resuspending the nuclei in the fetal bovine serum buffer; a filter; 4',6-diamidino-2-phenylindole; a deoxyribonucleic acid extraction kit for extracting deoxyribonucleic acid (DNA) from the nuclei; a single primer isothermal amplification kit; and, an endonuclease for fragmenting extracted DNA during the single primer isothermal amplification.

The kit may further comprise: a deoxyuradine triphosphate labeling kit; a reference sample; a comparative genomic hybridization array; a DNA shearer; an end repair and 3' adenylation kit; an indexed adapter configured to be ligated onto an adenosine-tailed strand of the sheared DNA; a DNA polymerase for amplifying a sheared DNA ligated to the indexed adapter; a paired end cluster generation kit; and/or exonic ribonucleic acid probes configured to selectively capture, for example by hybridization, a portion of the amplified DNA comprising an exon.

The invention is also directed to a method of selecting a therapy for a subject with cancer comprising identifying aberrations in a variable cancer cell genome derived from a formalin fixed paraffin embedded (FFPE) cancerous tumor sample and selecting an effective therapeutic agent to treat the cancer cell with the identified aberrations. In some embodiments, the aberration is mapped to the chromosomal region of 1p32-p31. The aberration may be mapped to the c-jun gene and may indicate that the cancer that is resistant to vemurafenib.

In certain aspects, the aberration may affect expression of an oncogene. The oncogene may be a growth factor, a receptor tyrosine kinase, a cytoplasmic tyrosine kinase, a cytoplasmic serine/threonine kinase, a regulatory subunit of a cytoplasmic serine/threonine kinase, a regulatory GTPase, or a transcription factor.

BRIEF DESCRIPTION OF THE FIGURES

The patent or application file contains at least one drawing executed in color. Copies of this patent or patent application publication with color drawing(s) will be provided by the Office upon request and payment of the necessary fee.

Illustrative and exemplary embodiments of the invention are shown in the drawings in which:

FIG. 6 shows the overlap of the whole exome sequence data for the cell line, amplified sorted FF, and amplified sorted FFPE samples derived from the same patient sample.

FIG. 8 shows an example of the overlap of ADM2 intervals in aCGH profiles of sorted FFPE PDA samples before and after amplification.

Figure 10:
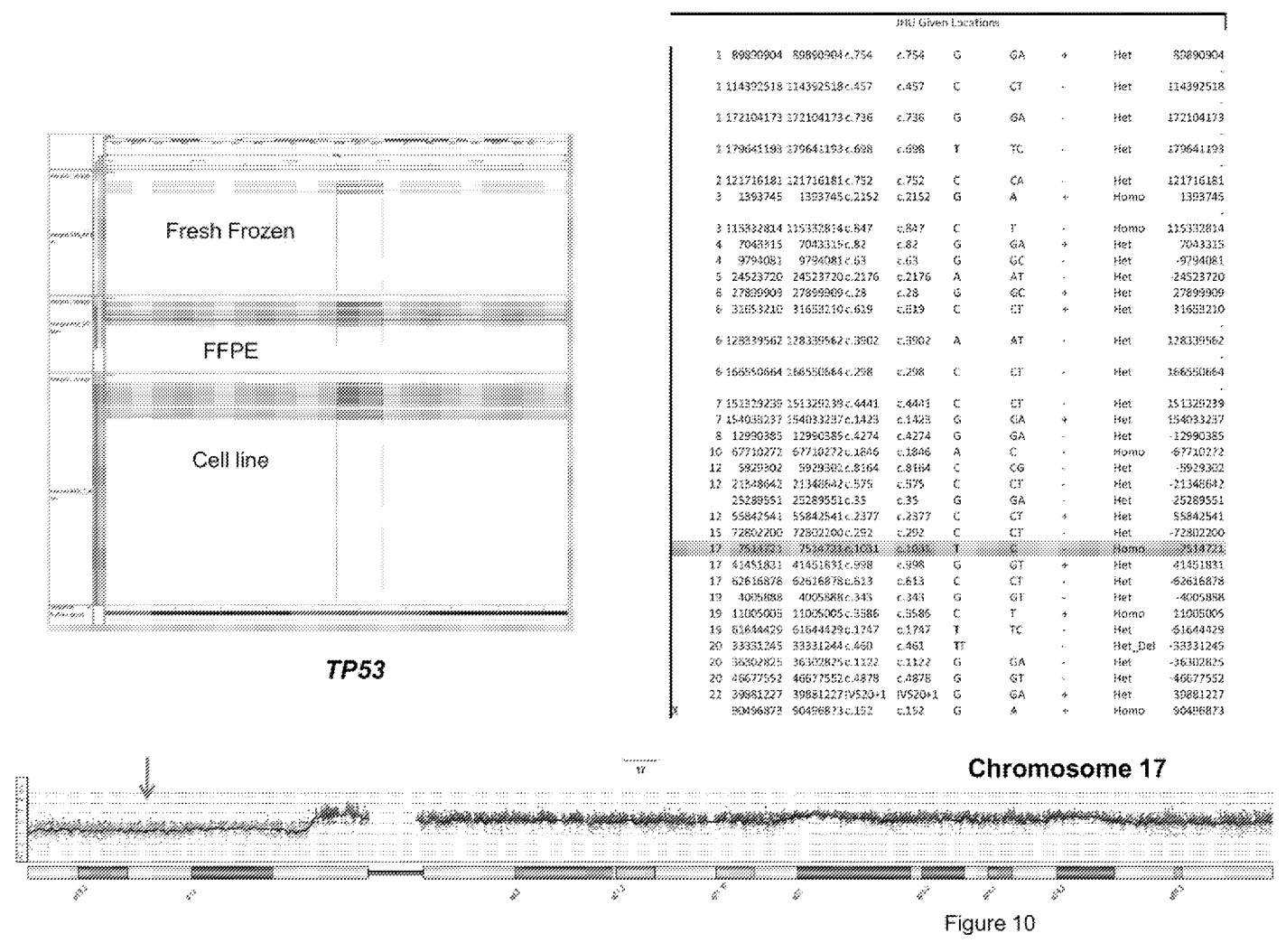

FIG. 10 shows the detection of a homozygous mutation in TP53 in the cell line, sorted FF and sorted FFPE PDA samples from the same tissue and the corresponding CGH plot of chromosome 17 with copy number loss at 17p.

FIG. 12 shows the detection of a heterozygous mutation in VWF in the cell line, sorted FF and sorted FFPE PDA samples from the same tissue and the corresponding CGH plot of chromosome 12 with copy number gain at 12p.

FIG. 13 shows the detection of a heterozygous mutation in KRAS in the cell line, sorted FF and sorted FFPE PDA samples from the same tissue and the corresponding CGH plot of chromosome 12 with copy number gain at 12p.

FIG. 14 shows the detection of a homozygous mutation in CTNNA3 in the cell line, sorted FF and sorted FFPE PDA samples from the same tissue and the corresponding CGH plot of chromosome 10.

whole genome plots of sorted 3.1N population, and C-D) chromosome 11 and gene level view of focal 11q13.3 amplicon that includes the CCND1 locus in 3.1N genome. Shaded areas denote ADM2-defined aberrant intervals.

Figure 22:
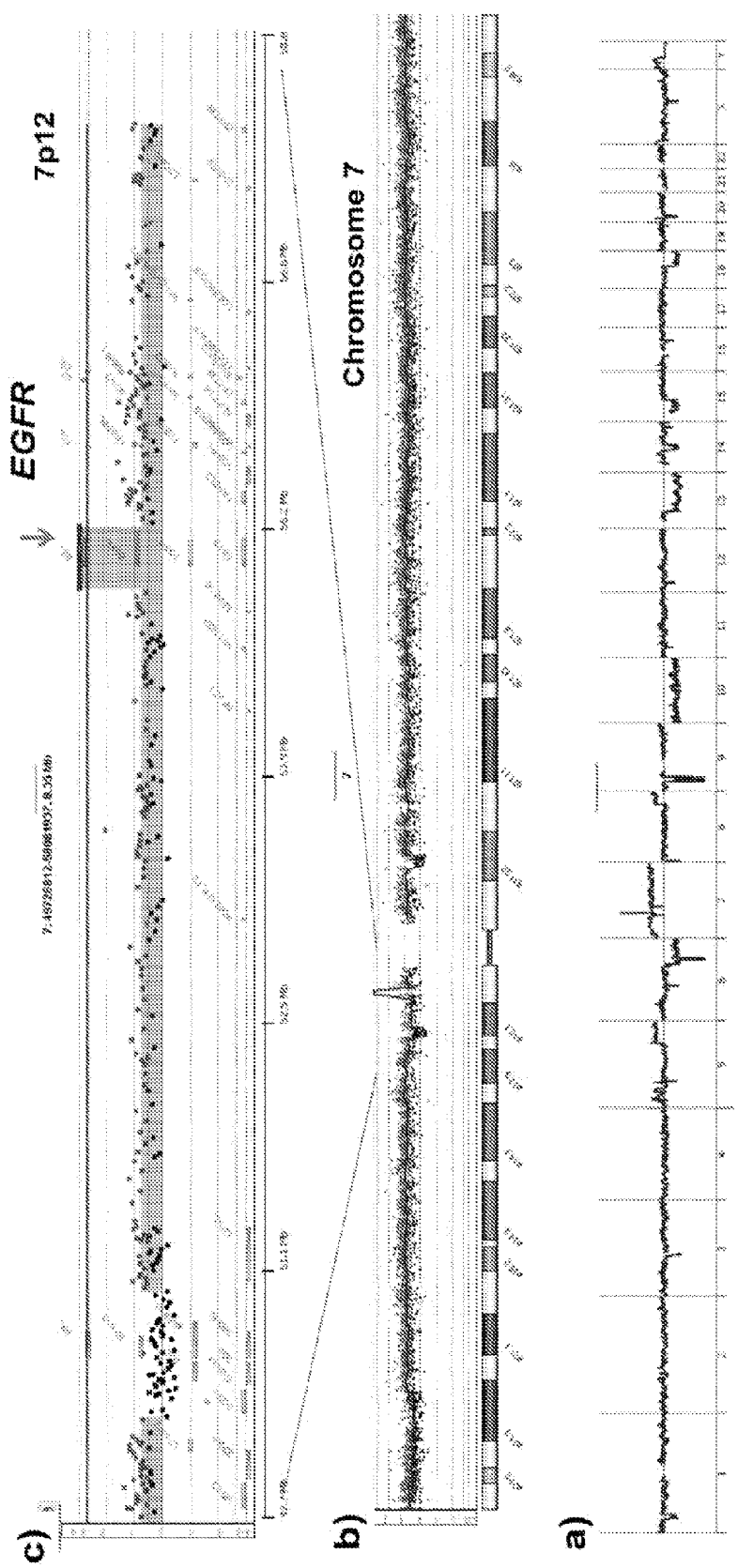

FIG. 22 depicts aberration detection and aCGH analysis of a flow sorted aneuploid population from glioblastoma multiforme formalin fixed paraffin embedded (FFPE) tissue: A) whole genome plots of sorted tumor population, and B-C) chromosome 7 and gene level view of focal 7p11 amplicon that includes the EGFR locus. Shaded areas denote ADM2-defined aberrant intervals.

Figure 23:
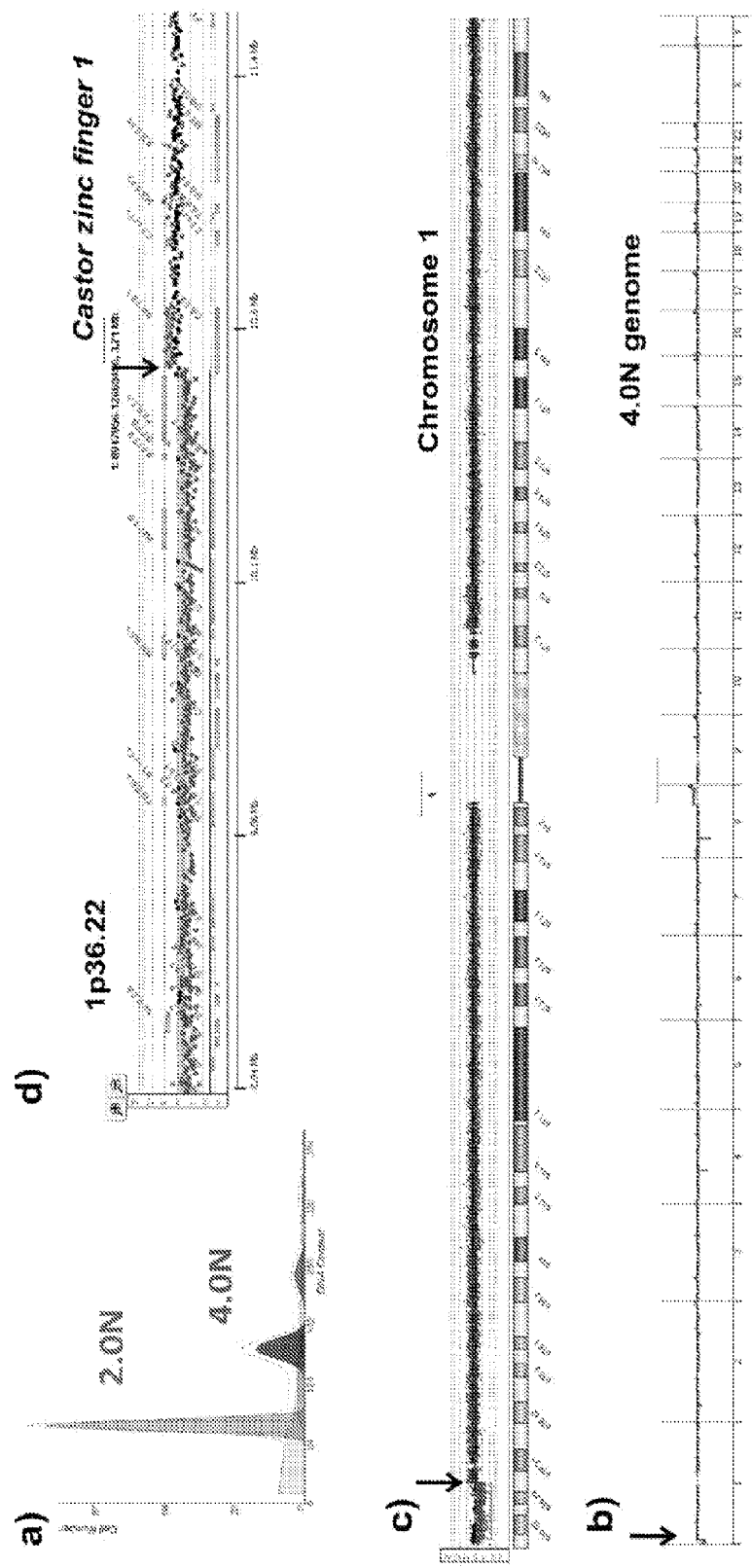

FIG. 23 depicts aberration detection and aCGH analysis of a flow sorted tetraploid population from small cell carcinoma of the ovary (SCCO) formalin fixed paraffin embedded (FFPE) tissue 006: A) diploid (blue) and tetraploid (red) populations sorted from the FFPE sample, B-C) whole genome and chromosome 1 aCGH plots of 4.0N genome, and D) gene view of 1p36.22 and mapping of breakpoint at CASZ1 locus. Shaded areas denote ADM2-defined aberrant intervals.

Figure 24:
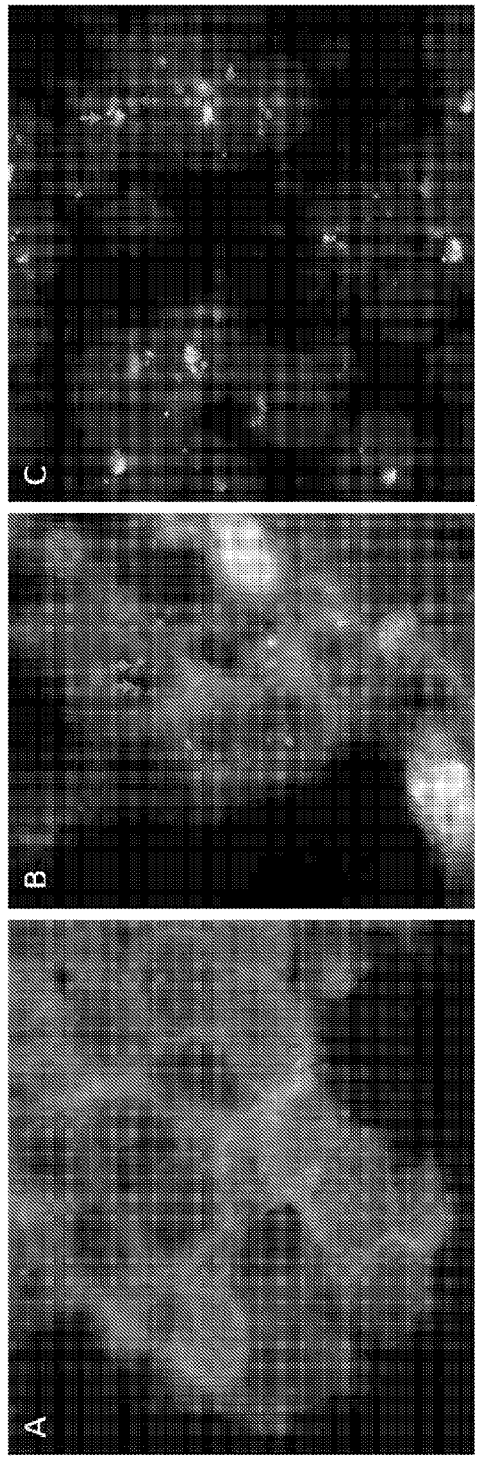

FIG. 24 depicts (fluorescence in situ hybridization) FISH validation of genomic aberrations detected by array CGH. A and B) FISH hybridization on the pancreatic adenocarcinoma B3733 where A) reveals a homozygous CDKN2A gene deletion, whereas the control pancreas tissue, and B) harbors two intact copies of the genes CDKN2A (green) and of the centromere 9 (red). Red and green arrows point towards centromere 9 and CDKN2A gene signals, respectively. In C) FISH hybridization with the Cyclin D1 FISH probe on the bladder carcinoma B33251 shows genomic amplification of the CCND1 gene (green arrow). Red and green arrows point towards centromere 11 and CCND1 gene signals, respectively.

Figure 25:
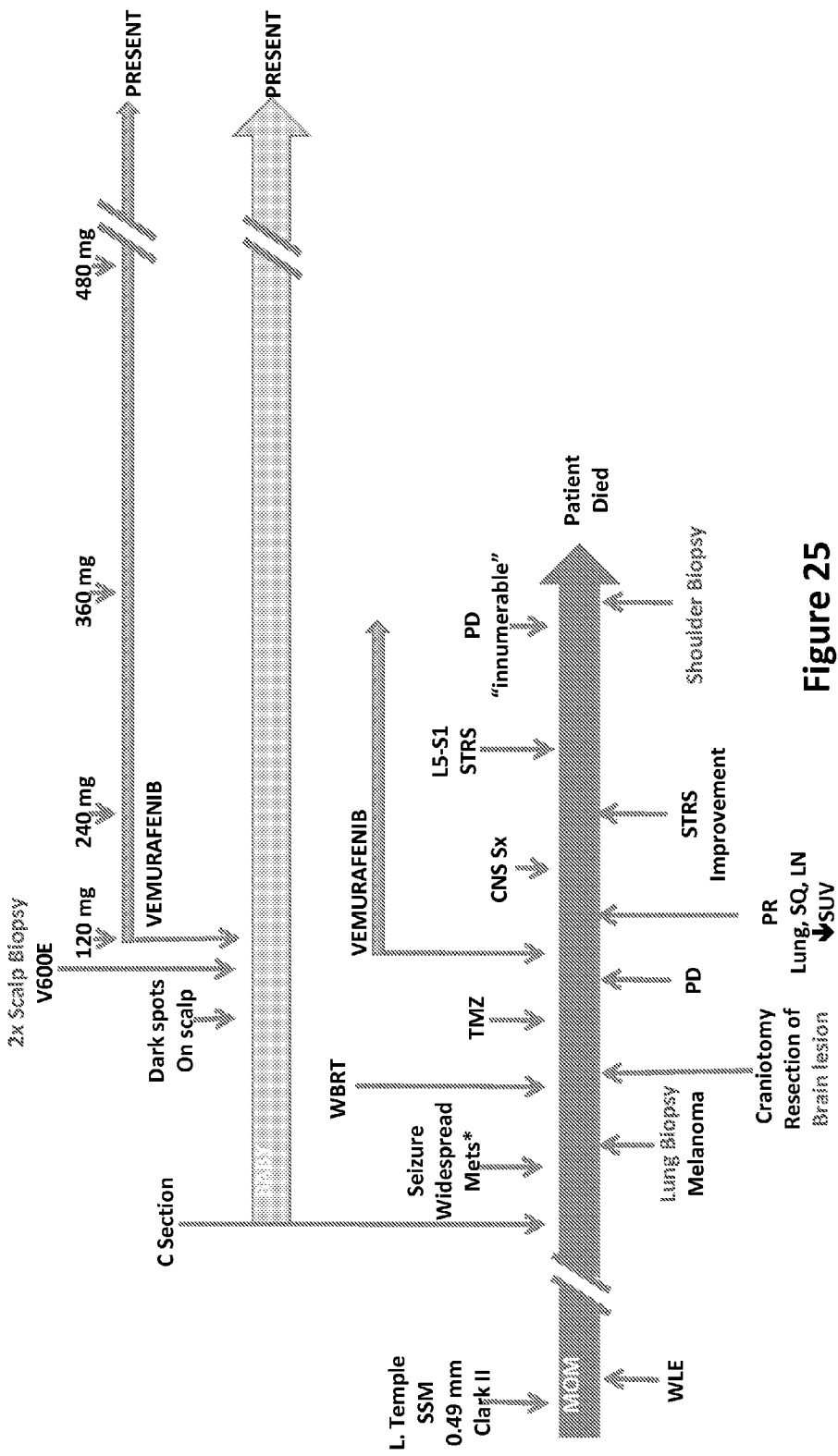

FIG. 25 shows a summary of the clinical history of a mother and infant diagnosed with melanoma and treated with vemurafenib.

Figure 26:
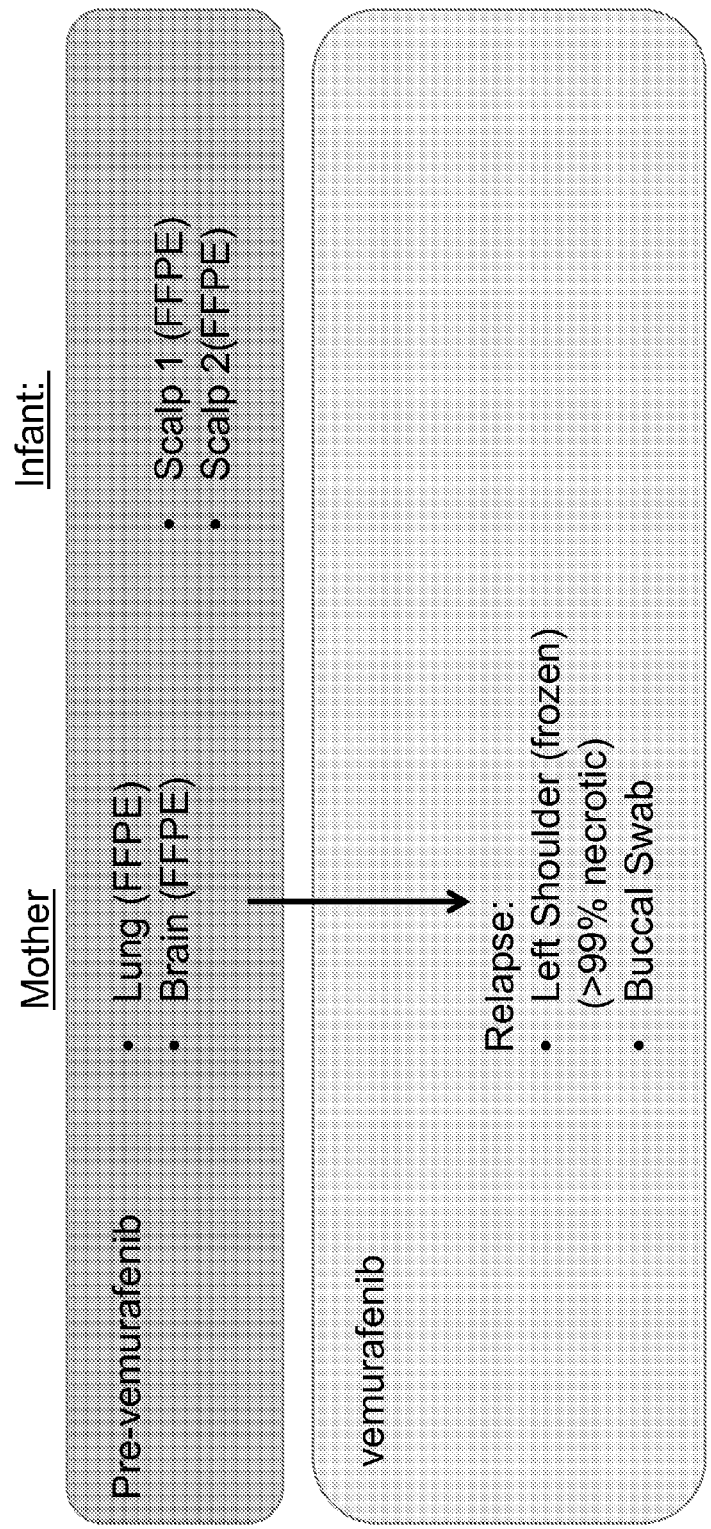

FIG. 26 shows tissues available for analysis pre- and post-vemurafenib treatment from the mother and infant.

Figure 27:
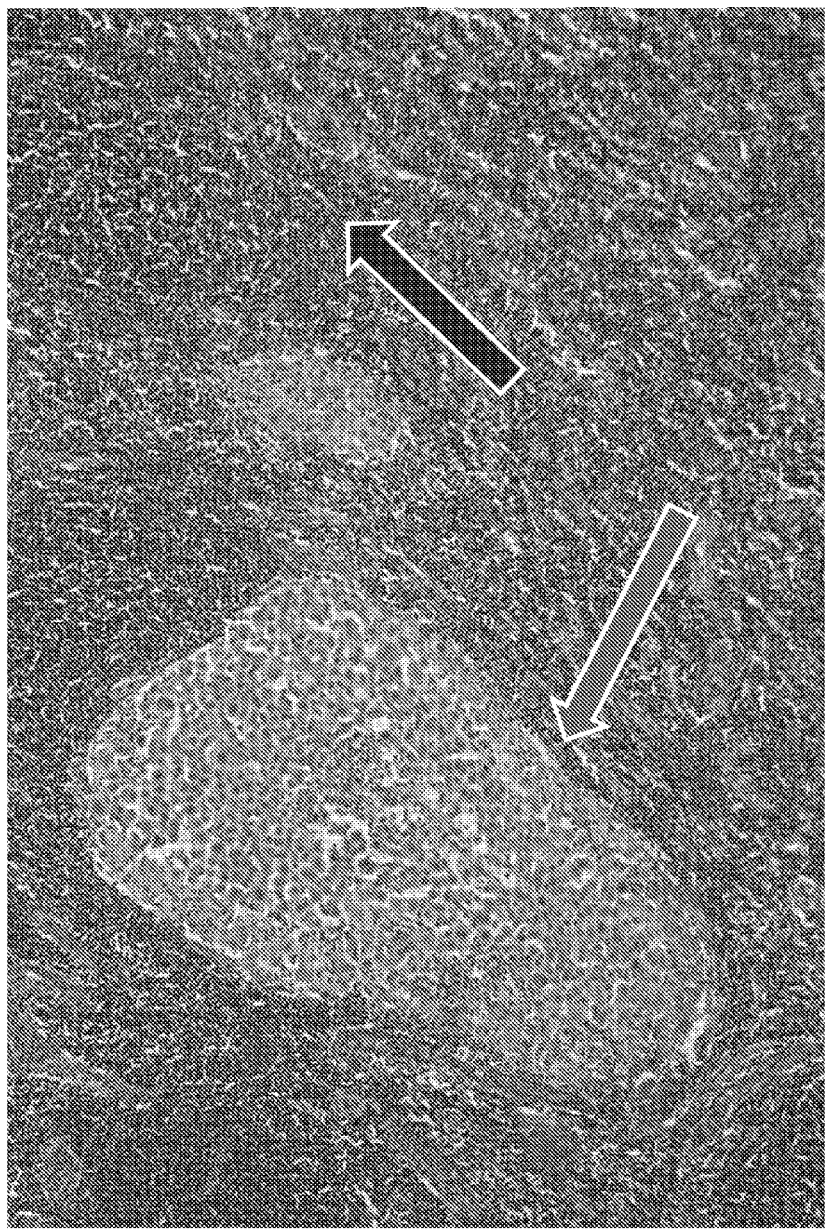

FIG. 27 depicts the complexity of the tissue samples from the mother and infant. Examples of a small metastatic melanoma in a sea of lymphocytes in a lymph node are indicated with arrows. Genomic profiling of such tissues is unlikely to identify aberrations present in the melanoma tissue without first sorting the sub-populations of cells.

Figure 28:
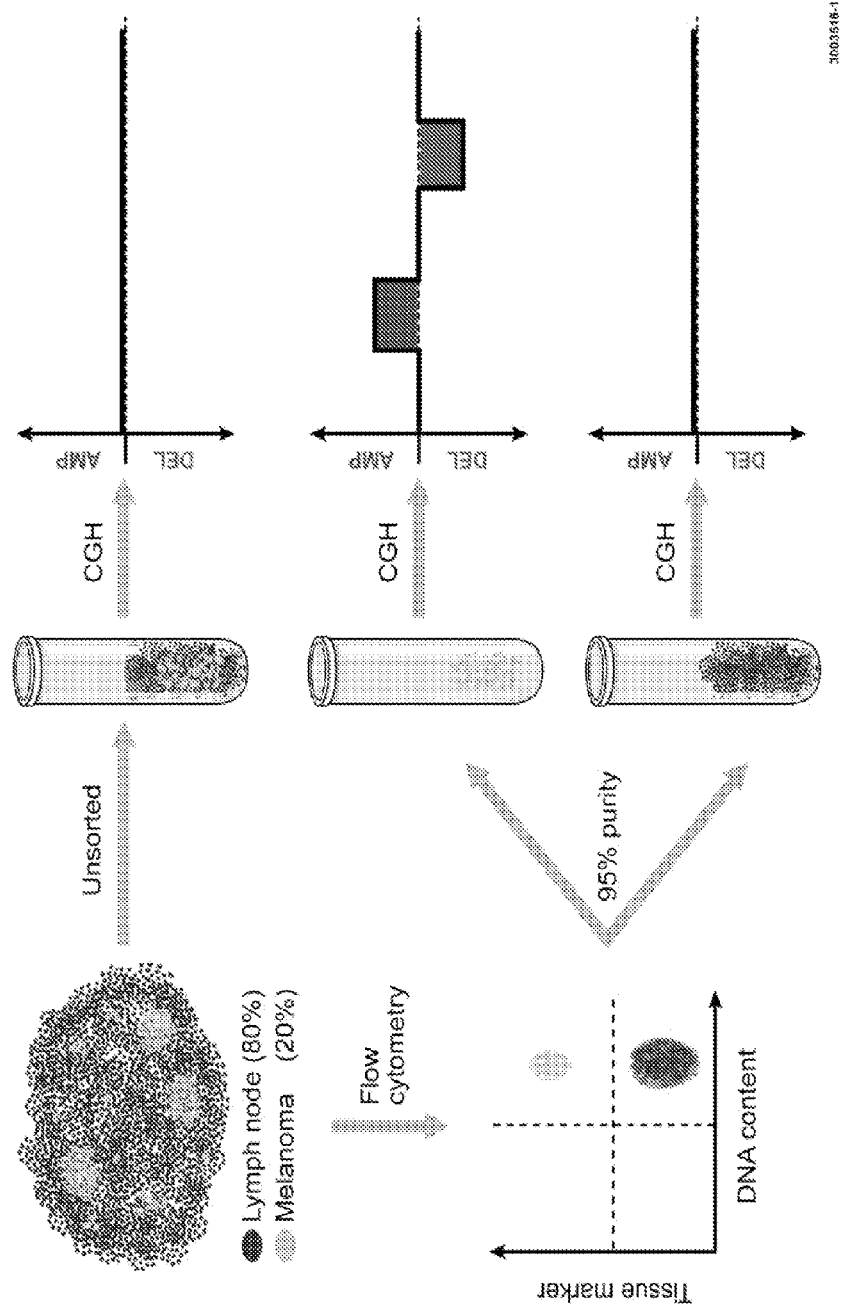

FIG. 28 depicts aCGH performed on unfractionated samples of melanoma metastases fails to detect any amplifications or deletions (upper portion of figure). With the aid of flow cytometry, melanoma nuclei (pink) are purified from lymph node cells (purple), which are then used for aCGH studies (lower portion of figure).

Figure 29:
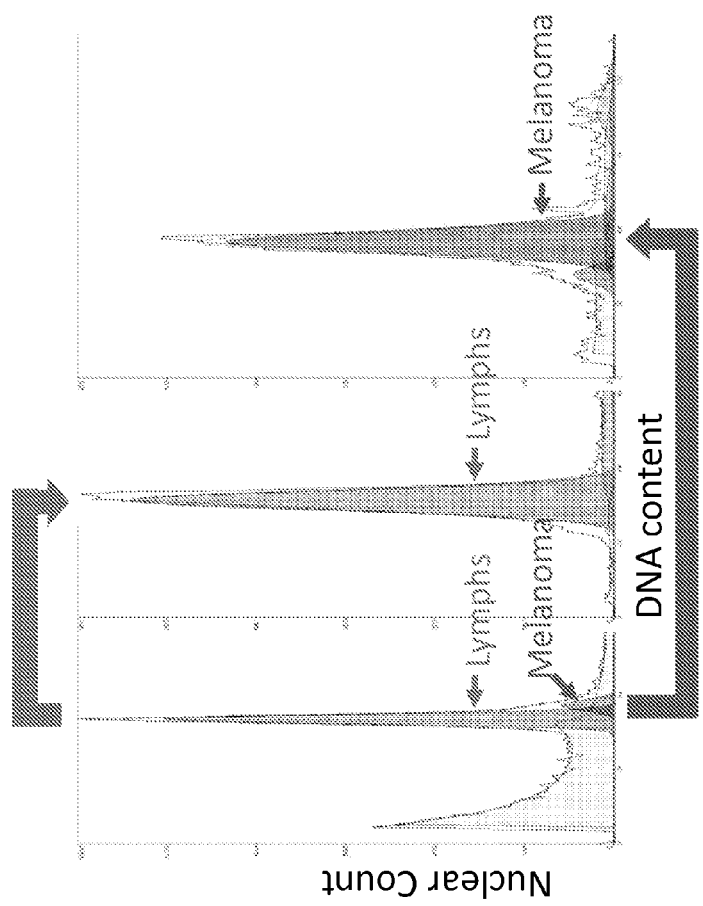

FIG. 29 depicts cell cycle modeling of the bulk tissue revealing a small population staining for melanocytic marker (red, left panel). Although the population of interest (red) comprises only 8% of overall nuclei in the studied tissue, flow separation allows high-level purification (over 95%) of the tumor population (red peak, right panel).

Figure 30:
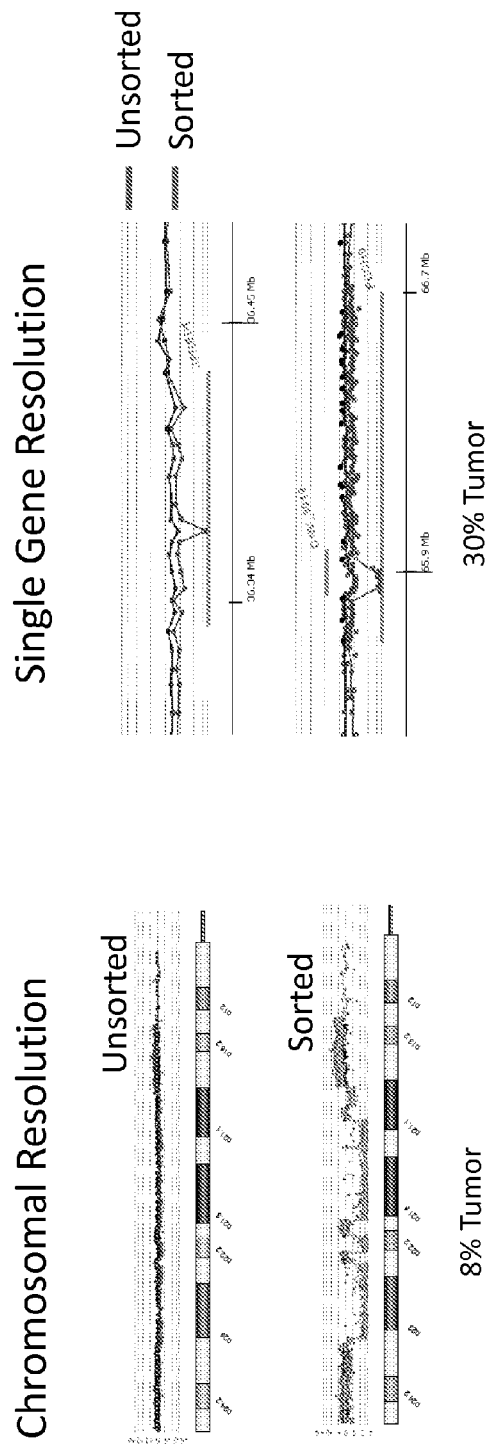

FIG. 30 depicts CGH of flow-sorted nuclei. Purified nuclei from typical mixed tumor specimens were utilized for CGH. Sorting led to enhanced resolution of genomic changes at both low (chromosomal) resolution as well as high (single gene resolution). LEFT: Analysis of unsorted tumor sample (upper tracing), in which tumor cells are only 8% of the sample failed to identify copy number abnormalities. However, purification of the tumor subset (lower tracing) clearly demonstrates several small homozygous deletions. RIGHT: In a second sample containing 30% tumor cells, no aberrations were detected in the unsorted sample (blue), while sorting (red) led to detection of small foci of loss at two different genomic regions, as illustrated in upper and lower panel, respectively.

Figure 31:
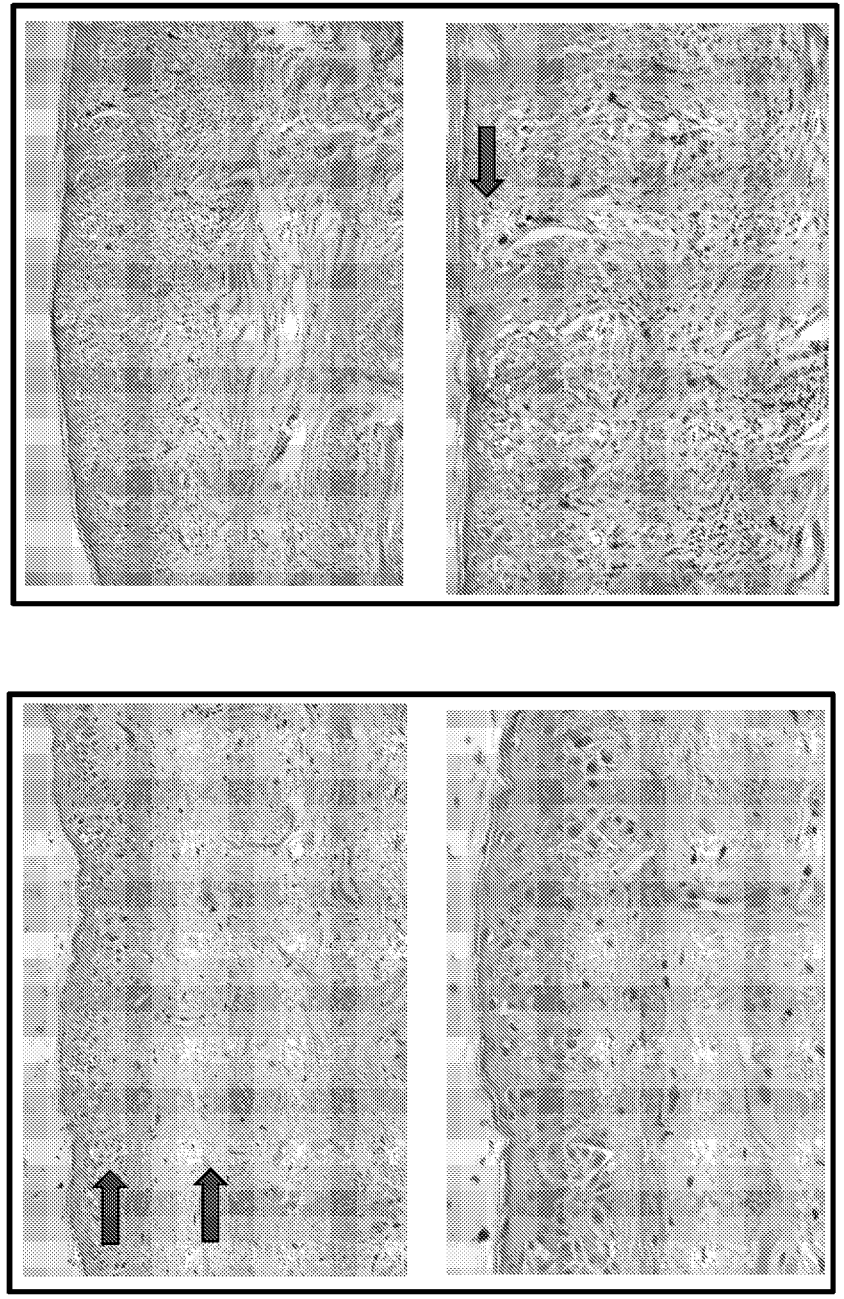

FIG. 31 depicts determination of clonality by histopathology. Examples of two small lesions are shown read out by pathology as primary melanomas. Although, these findings could be seen in the "epidermotropic" type of metastatic melanoma, the typical findings suggestive of such a metastatic process were not seen in any of the numerous biopsy tissues. Also shown are confluent melanocytes along the epidermal basal layer. No dermal melanocytes were identified. A band-like zone of severe solar elastosis is seen in the papillary dermis. These lesions were indistinguishable from MMIS, lentigo maligna type, but occurred as an epidermotropic metastasis in this patient.

FIG. 32 depicts a multiparameter nuclear flow analysis. An evaluation of 2 tumor populations (2 upper tracings) and 1 matched normal population (lower tracing) is shown. Note that an aberration found in all three samples (black arrows) is indicative of a germline polymorphism. Blue arrows indicate an amplification and a deletion seen in both tumor samples but not in the normal sample at the bottom. These data indicate that the two tumors were clonally related, thus, confirming the metastatic nature of the disease. The two tumor samples also contained additional, divergent aberrations, which were not shared. This is consistent with ongoing tumor evolution that continues after these clones diverged from the common progenitor.

Figure 33:
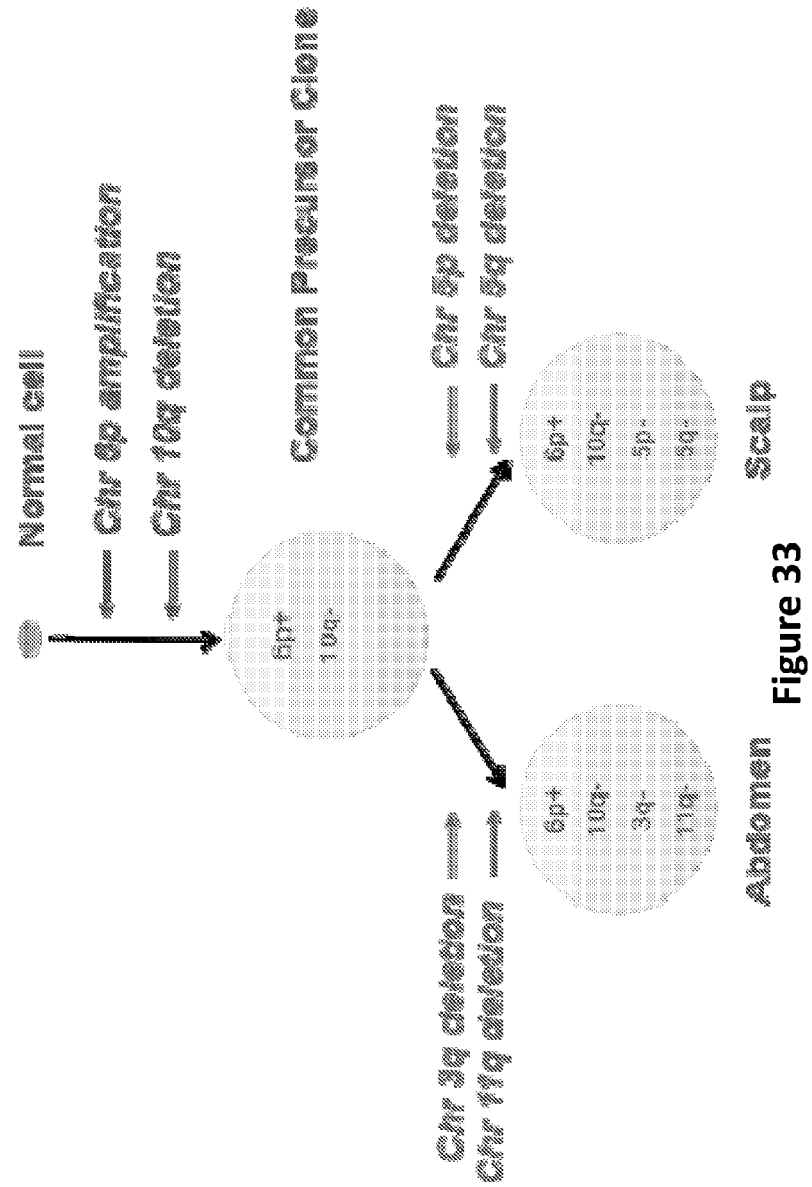

FIG. 33 depicts the genomic signature of the clonal progression. The patient's two melanomas shared 2 abnormalities on aCGH, a chromosome 6p amplification and a 10q deletion, supporting the notion of common clonal origin. As the tumors continued to develop, additional divergent abnormalities developed.

Figure 34:
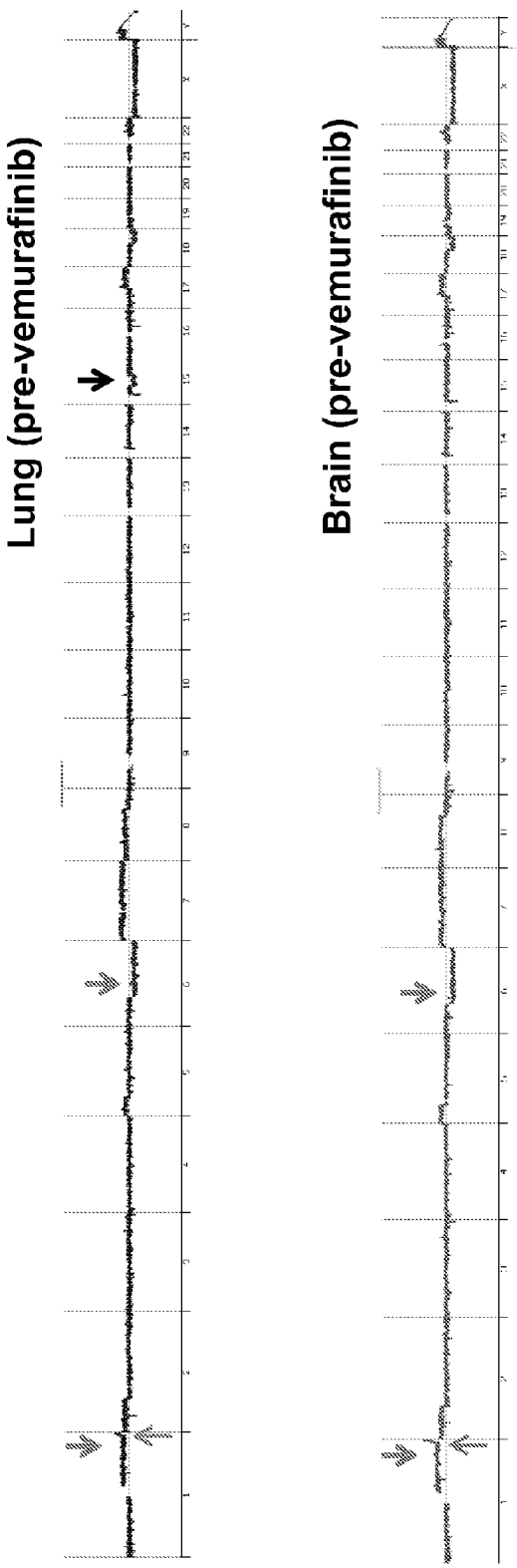

FIG. 34 depicts an aCGH analysis identifying at least two distinct melanoma populations in the mother.

Figure 35:
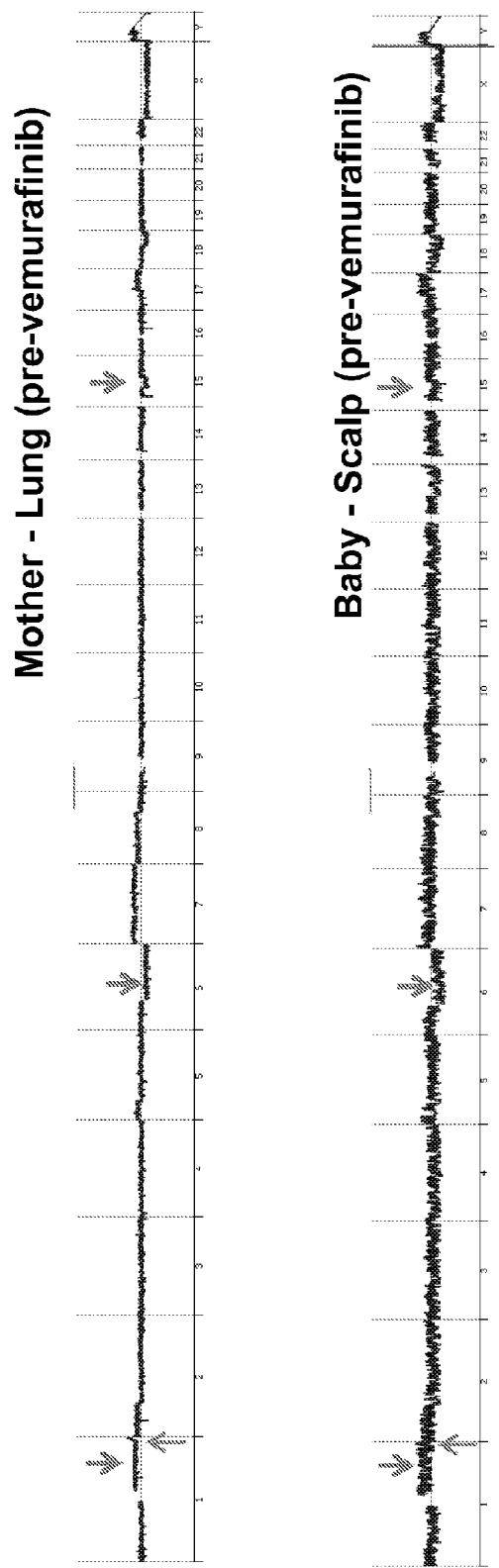

FIG. 35 depicts an aCGH analysis showing that the mother's lung lesion and infant's scalp lesions were related.

Figure 36:
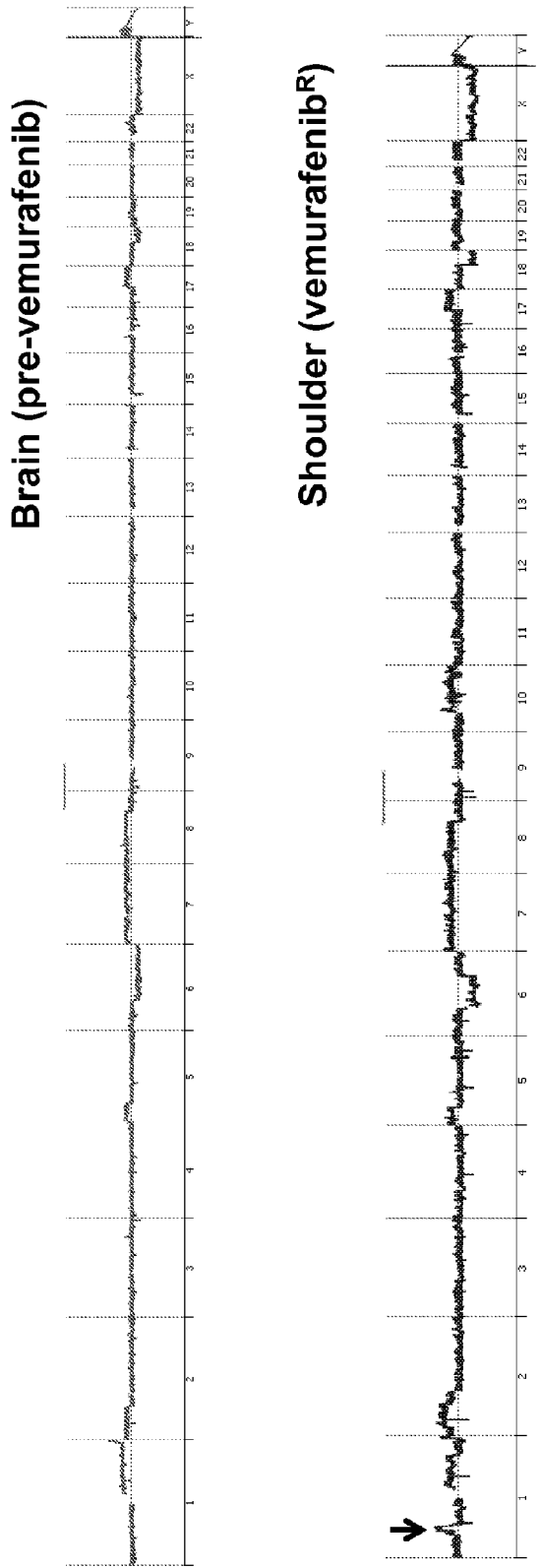

FIG. 36 depicts an aCGH analysis identifying a unique genomic aberration (black arrow) in the mother that induced resistance to vemurafenib (vemurafenib$^R$).

Figure 37:
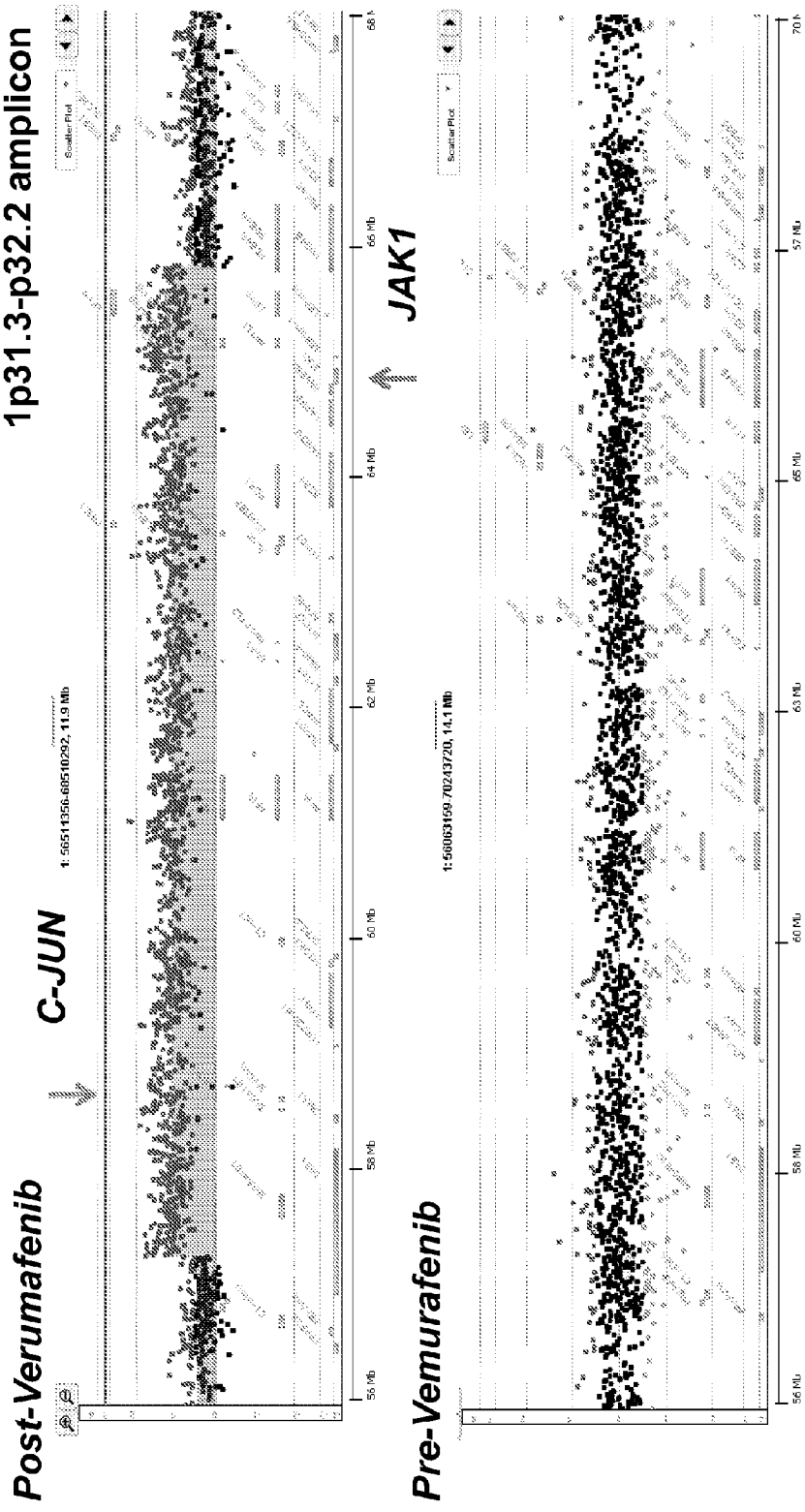

FIG. 37 depicts aCGH analyses identifying unique genomic aberration in the mother (i.e., C-Jun and Jak1).

Figure 38:
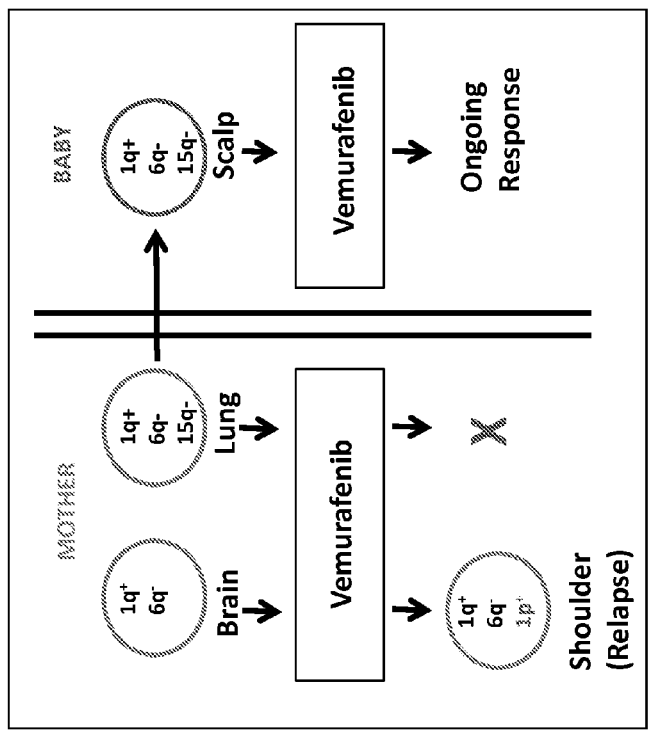

FIG. 38 depicts a CGH-based model of progression of the melanomas in the mother and infant. Genomic aberrations on specific chromosomes are indicated.

Figure 39:
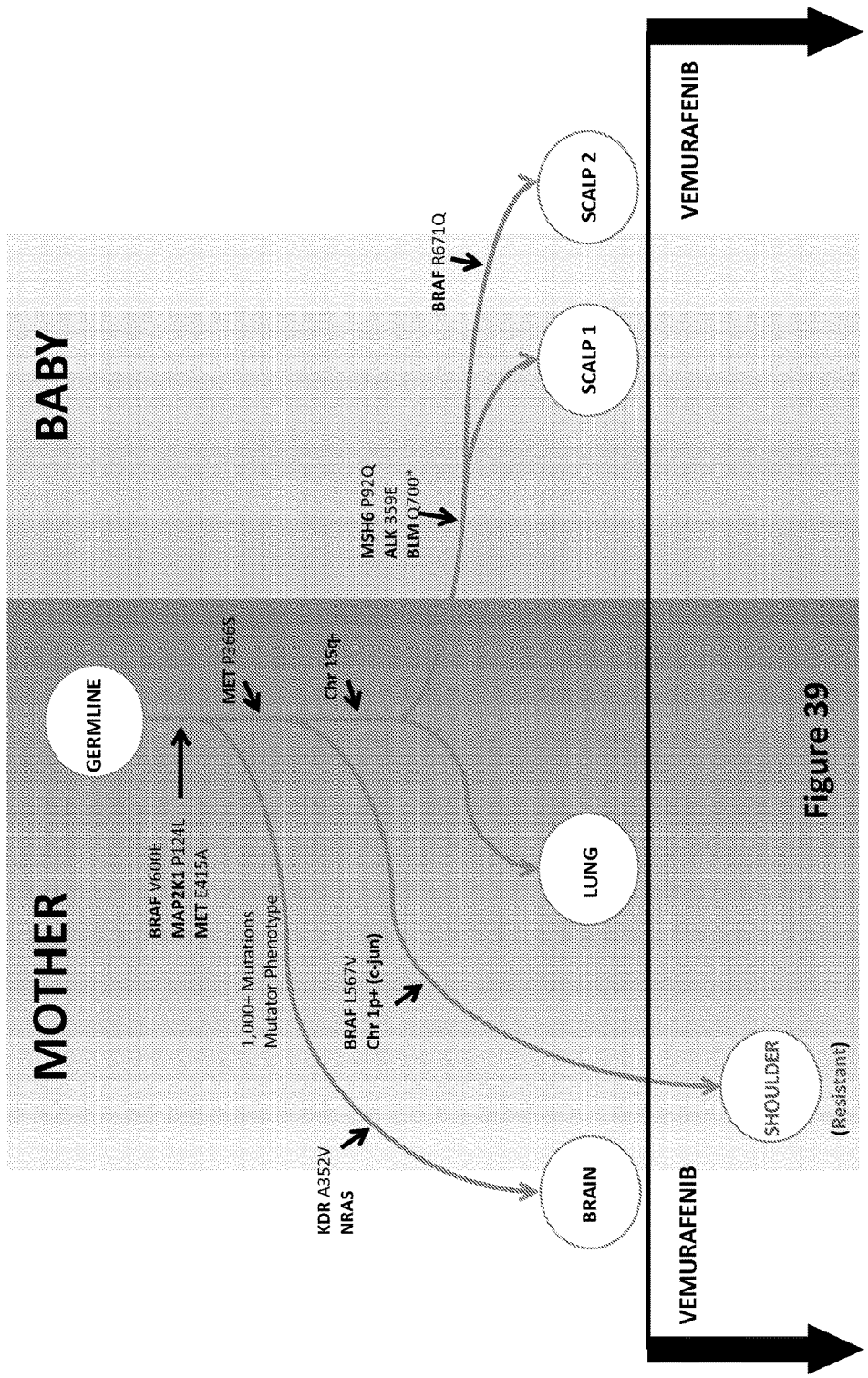

FIG. 39 depicts a CGH-based model of progression of the melanomas in the mother and infant. Specific genetic mutations are identified and mapped to the tumor samples analyzed.

Elements and facts in the figures are illustrated for simplicity and have not necessarily been rendered according to any particular sequence or embodiment.

DETAILED DESCRIPTION OF THE INVENTION

Aspects and applications of the invention presented here are described herein, in the figures and detailed description of the invention. Unless specifically noted, it is intended that the words and phrases in the specification and the claims be given their plain, ordinary, and accustomed meaning to those of ordinary skill in the applicable arts.

To optimize certain applications of preferred embodiments of the invention, the high definition genomic tools for the interrogation of FFPE samples flow cytometry expertise are applied to the preparation of highly purified material from routinely processed FFPE blocks. In some implementations, DNA content-based assays are used to identify and subsequently sort nuclei of diploid and aneuploid populations from a variety of archived tissue samples. DNA extraction and amplification protocols are optimized to provide high quality templates for both array comparative genomic hybridization (aCGH) and next generation sequencing (NGS) of each flow sorted FFPE tumor population.

In certain implementations, in order to assess the disclosed methods' ability to profile the genomes of this highly lethal cancer using archived FFPE samples, matching fresh frozen and FFPE pancreatic ductal adenocarcinoma (PDA) samples are used. A variety of solid tumor tissues, for example, triple negative breast carcinomas, melanomas, sarcomas, glioblastomas, and small cell carcinoma of the ovary, may be interrogated to validate the methods. In some implementations, a series of matching fresh frozen and FFPE samples are used, from a rapid autopsy PDA sample and a matching primary cell line with a previously published exome sequence to validate the use of sorted samples for NGS analysis. The ability to interrogate the genomes of objectively defined highly purified populations of tumor cells from FFPE samples with high definition aCGH and NGS provides a highly favorable approach to identify selected aberrations and deregulated signaling pathways that can be translated for improved patient outcomes. These methods have broad application for cancer research by enabling high definition studies of human tumors in vivo that can be used to advance effective more personalized therapies for cancer patients.

In contrast to conventional methods, the systems and methods disclosed herein provide whole genome and/or exome templates from sorted FFPE samples that can be used for high definition analyses of samples of interest. Increased inputs of DNA extracted from FFPE samples have been used to compensate for poor quality of template in labeling steps. Typically, 5 µg of DNA are required to provide sufficient labeled template for array experiments. Samples are typically selected and prepared based on gross morphology assessment using routine H&E staining. This greatly limits the use of FFPE for high definition genomics especially in solid tumors such as PDA a tumor type that is difficult to molecularly characterize at the biopsy level due to complex genomes and heterogeneous cellularity, as cancer cells represent, on average, only 25% of the cells within the tumor.

According to embodiments described herein, the sorting efficiencies can be significantly affected by the tissue type and quality. For FFPE samples, sorting efficiency can be decreased due to increased amounts of debris, aggregates, and sliced nuclei. To maintain sorting efficiencies at relatively high levels (about, e.g., >~60%, >~70%, >80%) the differential pressure between the core and the sheath fluids can be increased. In some implementations, however, the differential pressure between these two cannot be >1 in order to maintain high yield and purity of sorted samples. Flow sorting gates out debris that includes degraded nuclei. Slow sort rates and maintaining differential pressure of flow stream improves efficiency of sorts, and the overall yield of intact nuclei.

In some embodiments, to maintain an acceptable sorting efficiency, flow sorting rates and differential pressure are varied, in part, based on the variety and source of the tissue. In some embodiments, the flow sort rate is between about 50 and about 1500 events per second. In some embodiments, the flow sort rate is between about 100 and about 1000 events per second. In some embodiments, the flow sort rate is between about 300 and about 700 events per second. In some embodiments, the differential pressure of the flow stream (sheath/sample) is between about 0.1 and about 1.0. In some embodiments, the differential pressure of the flow stream is between about 0.4 and about 1.0. In some embodiments, the differential pressure of the flow stream is between about 0.6 and about 1.0. In some embodiments, an acceptable sorting efficiency is at least about 60%. In some embodiments, an acceptable sorting efficiency is at least about 70%. In some embodiments, an acceptable sorting efficiency is at least about 80%. In some implementations, the greatest variable in sorting is the origin of the tissue. Thus, according to embodiments, breast samples often sorted more efficiently than did pancreas samples regardless of whether they were FF or FFPE.

Figure 18:
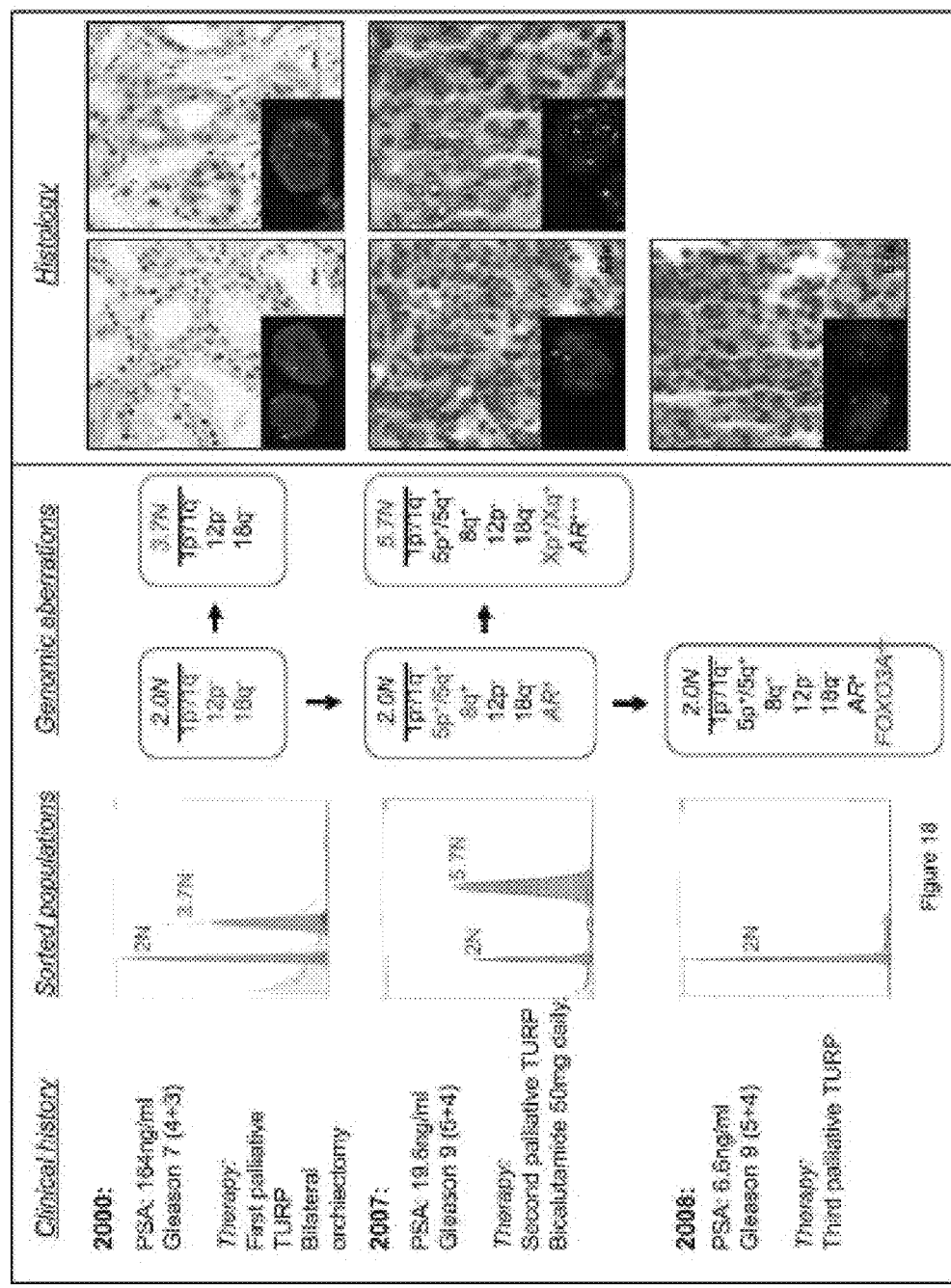
FIG. 18 depicts the pattern of clonal tumor populations during the evolution of castration resistant prostate cancer in a patient.
Figure 19:
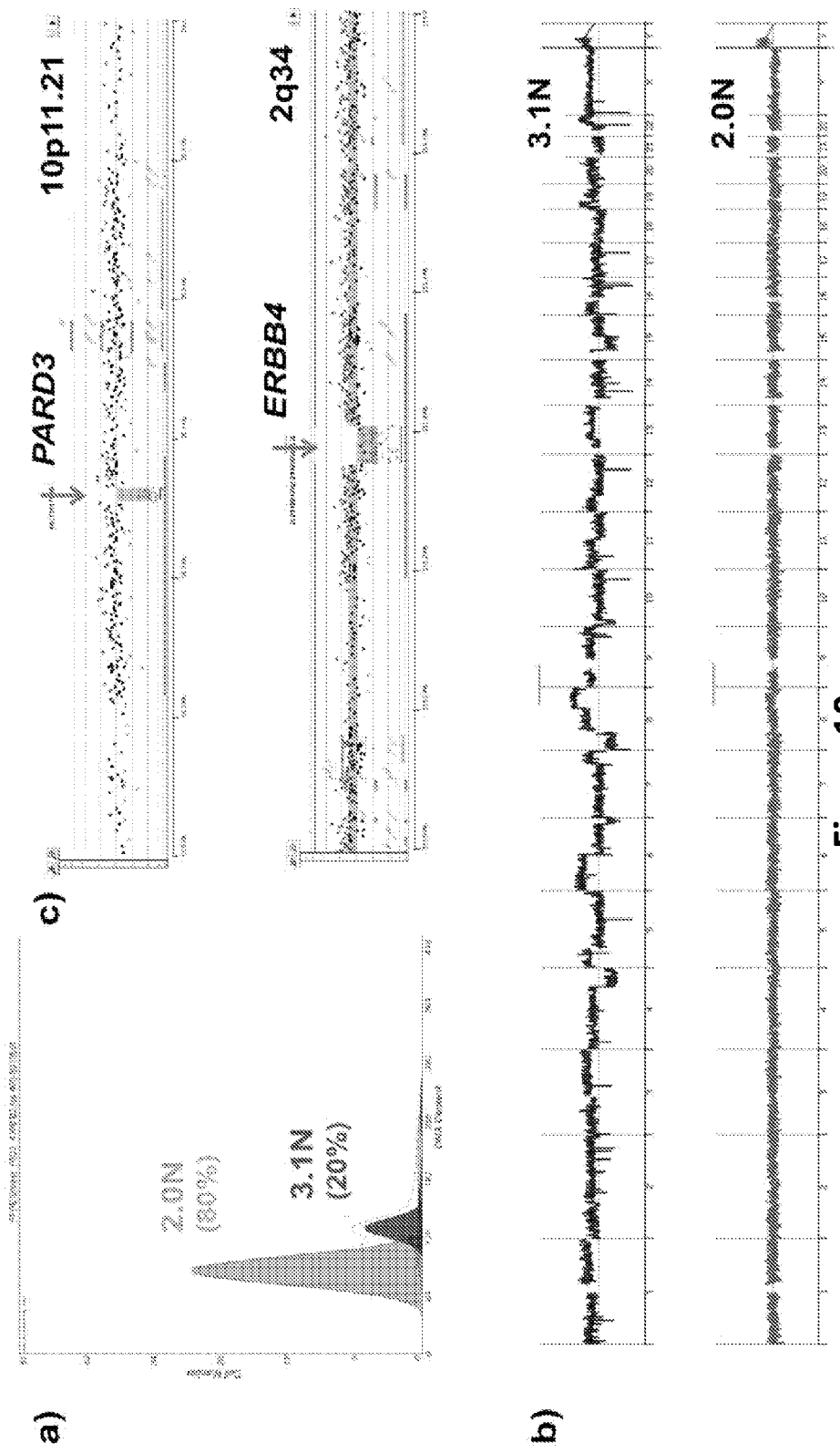
FIG. 19 depicts aberration detection and aCGH analysis of flow sorted diploid and aneuploid populations of triple negative breast cancer (TNBC) formalin fixed paraffin embedded (FFPE) tissue PS03 4398 B2: A) cell cycle and ploidy analysis of sorted 2.0N and 3.1N populations, B) whole genome plots of 2.0N and 3.1N sorted populations, and C) gene level view of focal deletions in PARD3 and ERBB4 genes in 3.1N genome. Shaded areas denote ADM2-defined aberrant intervals.
Figure 20:
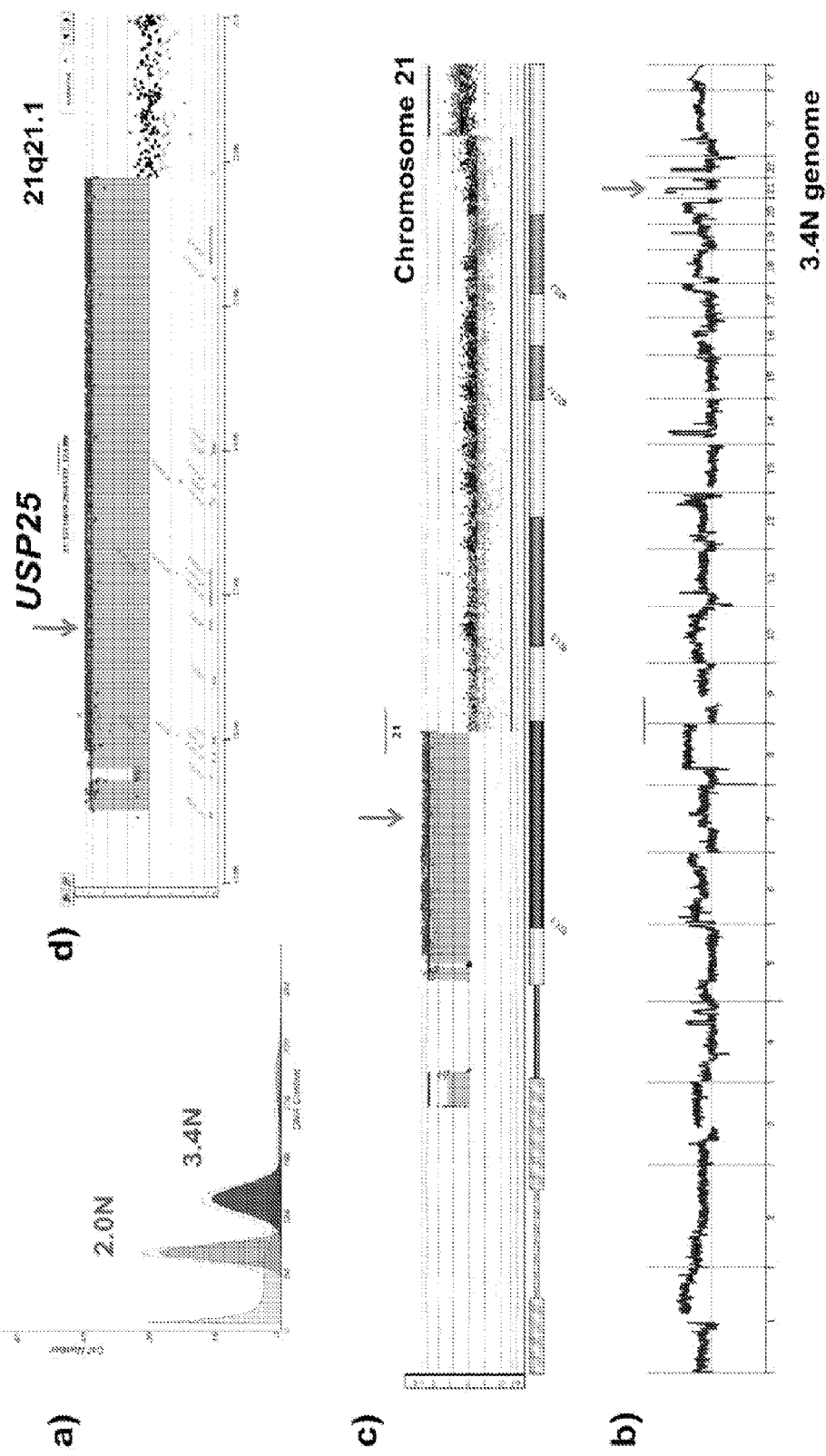
FIG. 20 depicts aberration detection and aCGH analysis of a flow sorted aneuploid population of triple negative breast cancer (TNBC) formalin fixed paraffin embedded (FFPE) tissue SS04 4239 A2: A) cell cycle and ploidy analysis of sorted 2.0N and 3.4N populations, B) whole genome plots of sorted 3.4N population, and C-D) chromosome and gene level view of focal 21q21.2 amplicon that includes the USP25 locus in 3.4N genome. Shaded areas denote ADM2-defined aberrant intervals.
Figure 21:
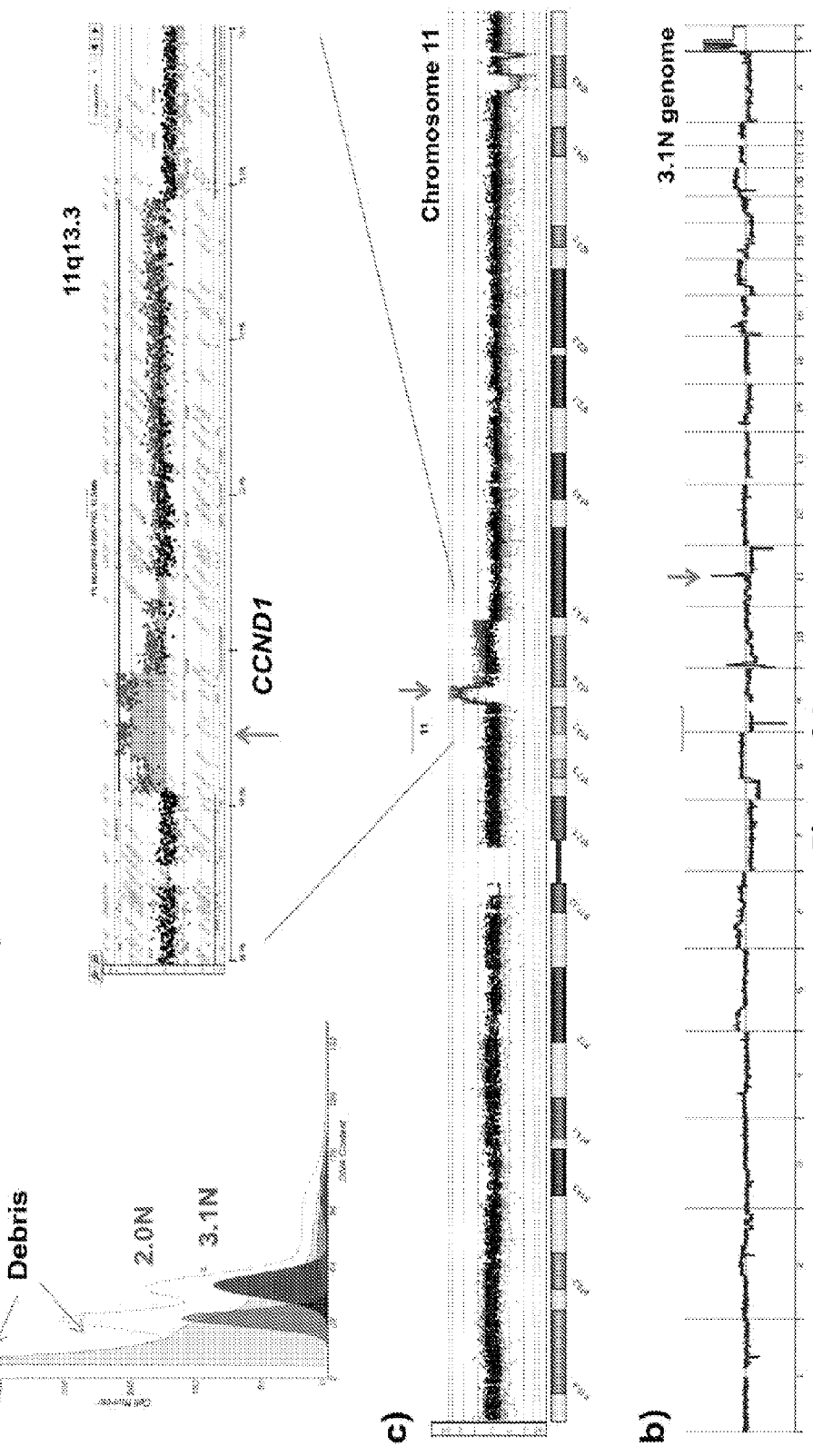
FIG. 21 depicts aberration detection and aCGH analysis of a flow sorted aneuploid population from bladder carcinoma formalin fixed paraffin embedded (FFPE) tissue B33251. Flow sorting of bladder carcinoma formalin fixed paraffin embedded (FFPE) tissue B33251: A) cell cycle and ploidy analysis of sorted 2.0N and 3.1N populations, B)

In some implementations, gating based on DNA content provides a robust quantitative measure to identify and subsequently sort tumor populations from samples of interest. For example a 3.0N population sorted from a FF PDA sample was detected over 3 years later in an FFPE sample from the same tissue, as shown in FIG. 18. The distribution and the ploidy of each population present can be determined by fitting the $G_0/G_1$ and $G_2/M$ peaks of each population as Gaussian curves and the S phase distribution as a Gaussian broadening distribution. The DNA content histograms from tumor tissue are typically not optimal (broad CV's, high debris and aggregation) or are complex (multiple overlapping peaks and cell cycles) with frequent skewing and non Gaussian peak shapes. This is even truer when analyses are derived from formalin fixed specimens.

Furthermore, in some embodiments, most nuclear suspensions analyzed by DNA content flow cytometry contain some damaged or fragmented nuclei (debris) resulting in events usually most visible to the left of the diploid $G_0/G_1$ peak and fall rapidly to baseline. The shape of most debris curves is not exponential. For reproducible phase measurements, at least 8,000, more preferably at least 9,000 or 10,000, events are typically required. However, if a substantial proportion of events are from debris or aggregates, the total number of events acquired should be correspondingly higher in order to assure the required minimum number of intact single nuclei for accurate curve fitting.

In some implementations, sorting provides preparations of intact nuclei prior to extraction. This cleans up the sample prior to preparing DNA templates for whole genome analysis and preparation, and eliminates the need to preselect samples based on high levels (e.g., >60-70%) of tumor content for molecular analyses. In contrast the disclosed systems and methods use highly quantitative and objective measures to identify and subsequently purify tumor cell populations from samples of interest regardless of the initial tumor content. This methodology eliminates potential errors in sampling, due to non-quantitative morphology measures of biopsies, and greatly increases the number of samples that can be used for high definition genome analyses.

The use of short DNAse 1 digestion provides uniform templates for labeling from FFPE material.

The resolution of copy number analysis can be accurately defined as the per probe error in the detection of single copy number changes. This can be calculated by plotting the $\log_2$ ratios for all chromosome X probes in the following series of comparisons XY/XX versus XX/XX, and XX/XY. The overlap of the distributions for each histogram for the $\log_2$ ratios of chromosome X probes represents the error rate in distinguishing single copy number loss.

The resolution of the disclosed assays with highly purified sorted samples enables the discrimination of single copy loss from homozygous loss using a rigorous cut off of $\log_2$ ratio <−3.0 in each tumor genome. Furthermore, the relatively low error rates in the disclosed assays provide high resolution of mapping amplicon and deletion boundaries throughout the genome. (See, e.g., FIGS. 7-14). Thus, rather than estimating resolution as a function of probe and measurement density for a given assay, the resolution of each measurement has been optimized in the disclosed whole genome assays. This is an essential feature in the application of both FF and FFPE samples for high precision measurements that can advance effective more personalized therapies for patients with cancer.

All fresh frozen samples were collected in liquid nitrogen and stored at −80° C. All tumor samples were histopathologically evaluated prior to analysis.

FFPE Sample Preparation and Flow Sorting

According to embodiments, FFPE samples are prepared for flow sorting. In some implementations, excess paraffin is removed with a scalpel from either side of each 40-60 µm scroll (e.g., a 40-60 µm scroll), which are then sectioned into 3 or 4 pieces each, depending on tissue size. Sectioning samples reduces accumulation of debris during the sorting process. Each sectioned piece is collected into individual microcentrifuge tubes then washed, for example, 3 times, with Xylene (e.g., 1 mL) for about 5 minutes to remove remaining paraffin. Each sample is rehydrated, for example, with sequential ethanol washes (100% 5 minutes×2, then 95%, 70%, 50% and 30% ethanol).

Each rehydrated sample is washed, by way of example, 2 times in 1 mL 1 mM EDTA pH 8.0. In some implementations, a 1 mL aliquot of 1 mM EDTA pH 8.0 is added to the samples and incubated at about 95° C. for about 80 minutes to facilitate the removal of protein cross-links present in FFPE tissue. Samples are then cooled to room temperature for more than about 5 minutes, followed by addition of, for example, 300 µL PBS 7.4 and gentle centrifugation for about 2 minutes at about 3.6 ref. The supernatant is removed and the pellet washed, for example, 3 times with 1 mL PBS 7.4/0.5 mM $CaCl_2$ to remove EDTA.

In some implementations, each sample is digested overnight (e.g., 6-17 hours) in 1 mL of a freshly prepared enzymatic cocktail containing, for example, 50 units/mL of collagenase type 3, 80 units/mL of purified collagenase, and 100 units/mL of hyaluronidase in PBS ph7.4/0.5 mM $CaCl_2$ buffer. Each enzyme is rehydrated with PBS ph7.4/0.5 mM $CaCl_2$ buffer immediately prior to addition to the cocktail mixture. Following overnight digestion about 500 µL NST is added to each sample to facilitate pelleting. Samples are centrifuged for about 5 minutes at about 3000 rcf, after which pellets are resuspended in about 750 µL of NST/10% fetal bovine serum and then passed through a needle (e.g., a 25 G needle) several times (e.g., 10-20 times).

In some implementations, the samples are filtered through a 35 µm mesh and collected into a 5 mL polypropylene round bottom tube. The mesh is rinsed with an additional amount, for example, 750 µl of NST/10% fetal bovine serum and placed on ice. According to embodiments, the total volume in the tube for each sample is approximately 1.5 mL. An equal volume of 20 ug/mL DAPI is added to each tube to achieve a final concentration of 10 ug/mL DAPI prior to flow sorting with a BD Influx cytometer with ultraviolet excitation (Becton-Dickinson, San Jose, Calif.). In some implementations, settings for sorting FFPE samples with the Influx sorter are as follows: drop formation is achieved with a piezzo amplitude of 6-10 volts and a drop frequency of 30 khertz. The sort mode is set to purity yield with a drop delay of 31.5-32. Sheath fluid pressure is typically 17-18 psi with a 100 µm nozzle. For single parameter DNA content assays, by way of example, DAPI emission are collected at >450 nm. DNA content and cell cycle are then analyzed using a software program, for example, MultiCycle (Phoenix Flow Systems, San Diego, Calif.).

DNA Extraction

In some implementations, DNA from sorted nuclei is extracted using a protocol, such as an amended protocol from QIAamp® DNA Micro Kit from Qiagen (Valencia, Calif.). By way of example and to briefly illustrate the amended protocol, each sorted sample is resuspended in 180 µl buffer ATL and 20 µl proteinase K then incubated for 3 hours at 56° for complete lysis. Samples are bound and washed according to QIAamp® DNA Micro Kit instructions, eluted into 50 µl of dd$H_2O$, then precipitated overnight with 5 µl sodium acetate and 180 µl 100% EtOH. Each sample is then centrifuged for 30 minutes at 20,000×g, washed in 1 mL of 70% EtOH for 30 minutes at 20,000×g. The samples are decanted and the DNA pellet is dried by speed vacuuming then resuspended in a small volume (e.g., 10-50 µL) of $H_2O$ for final concentrations suitable for accurate quantization.

DNA Amplification

According to embodiments, genomic DNA from sorted FFPE samples is amplified, for example, with single primer isothermal amplification. For example, in some implementations, the Ovation® WGA FFPE System from NuGEN® Technologies (San Carlos, Calif.) is used. DNA is processed in accordance with Ovation® WGA FFPE standard protocol with an alternate fragmentation step. In some implementations, resulting amplified product is used as template for aCGH analysis. In some implementations, resulting amplified product is processed, for example, with the NuGEN Encore ds-DNA module according to the suppliers instructions in order to generate double-stranded end repaired DNA as input for library suitable for next generation sequencing.

In some implementations, where fresh frozen samples are used to validate results extracted fresh frozen sourced genomic DNA is amplified using the phi29 based Illustra GenomiPhi V2 Amplification kit (GE Healthcare Bio-Sciences Corp., Piscataway, N.J.) according to published protocols. Validation is often performed when calibrating or experimenting with a protocol such as the disclosed methods; however, when the method is used to profile vast libraries of FFPE material, it is understood that fresh frozen samples are frequently not available, thus, acts associated with corresponding fresh frozen samples may be omitted. In some implementations, a 100 ng aliquot of Promega sourced female DNA is amplified with the matching amplification protocol to generate a suitable reference for each aCGH experiment using amplified DNA template. In some implementations, the amplification product quality is assessed by gel electrophoresis.

CGH Analysis

According to embodiments, comparative genomic hybridization analysis is performed. In some implementations, fresh frozen phi29 amplified and FFPE non-amplified DNAs are treated with DNAse 1 prior to Klenow based labeling. In some implementations, high molecular weight phi29 templates are digested for 30 minutes while the smaller fragmented FFPE samples are digested for only 1 minute. In each case, 1 µl of 10×DNase1 reaction buffer and 2 µl of DNase I dilution buffer were added to 7 µl of DNA sample and incubated at room temperature then transferred to 70° C. for 30 minutes to deactivate DNase I. In contrast, the amplified FFPE sourced DNAs do not require DNase 1 treatment prior to Klenow-based labeling. Sample and reference templates are labeled with Cy-5 dUTP and Cy-3 dUTP respectively, for example, using a BioPrime labeling kit (Invitrogen, Carlsbad, Calif.) according to published protocols.

In some implementations, labeling reactions are assessed using a Nanodrop assay (Nanodrop, Wilmington, Del.) prior to mixing and hybridization to CGH arrays, for example, 400 k CGH arrays (Agilent Technologies, Santa Clara, Calif.) for a period of time (e.g., 40 hours) in a rotating 65° C. oven.

In some implementations, microarray slides are scanned, for example, using an Agilent 2565C DNA scanner and the images are analyzed, for example, with Agilent Feature Extraction version 10.7 using default settings. In some implementations, the aCGH data is assessed with a series of QC metrics then analyzed using an aberration detection algorithm (ADM2) (18). In some implementations, the latter identifies all aberrant intervals in a given sample with consistently high or low log ratios based on the statistical score derived from the average normalized log ratios of all probes in the genomic interval multiplied by the square root of the number of these probes. This score represents the deviation of the average of the normalized log ratios from its expected value of zero and is proportional to the height h (absolute average log ratio) of the genomic interval, and to the square root of the number of probes in the interval.

Exome Library Preparation

According to embodiments, an exome library is prepared. In some implementations, 3 µg of high quality genomic DNA with a 260/280 ratio between 1.8 and 2.1 are fragmented to a target size of 150 to 200 bp, for example, on the Covaris E210 system (Woburn, Mass.). In some implementations, fragmentation is verified on a 2% TAE gel and fragmented samples are end repaired, for example, using New England Biolab's NEB Next kit (Ipswich, Mass.). In some implementations, repaired samples are adenylated at the 3' end, for example, using the NEBNext kit. In some implementations, adapters, such as Illumina (San Diego, Calif.) indexed adapters, are ligated onto A-tailed products. Samples are PCR amplified, for example, using Herculase II polymerase and purified. In some implementations, samples are then run, for example, on the Agilent Bioanalyzer to verify amplification and to quantify samples. In some implementations, by way of example, samples are adjusted to 147 ng/µl for a 24 hour hybridization to exonic RNA probes, for example, using Agilent's SureSelect All Exon 50 Mb Plus kit, which contains 561,823 probes targeting 202,124 exons. Captured products are next selected for, purified, and PCR amplified. Final libraries are verified and quantified, for example, using the Agilent Bioanalyzer.

Whole Genome Library Preparation

According to embodiments, a whole genome library is prepared. In some implementations, 1 µg of high quality genomic DNA with a 260/280 ratio between 1.8 and 2.1 is fragmented to a target size of 300-400 bp on, for example, the Covaris E210 System. In some implementations, fragmentation is verified on a 2% TAE gel. The fragmented sample is processed, for example, using Illumina's TruSeq DNA Sample Prep Kit-A. In some implementations, fragmented samples are end-repaired, adenylated on the 3' end, and ligated to paired-end adapters, such as Illumina adapters. Ligation products are purified, size selected at 400 and 450 bp, and PCR amplified and purified. Libraries are validated, for example, on the Agilent Bioanalyzer.

Paired End Next Generation Sequencing

In some implementations, libraries are denatured, for example, using 2N NaOH and diluted, for example, with HT2 buffer (Illumina). In some implementations, 1% of denatured and diluted phiX is spiked into each lane to allow for error rate reporting. In some implementations, cluster generation is performed, for example, using Illumina's cBot and HiSeq Paired End Cluster Generation Kit. Flowcells are paired end sequenced, for example, on Illumina's HiSeq 2000 using Illumina's HiSeq Sequencing Kit.

In some implementations, raw sequencing data are obtained, for example, from the Illumina HiSeq 2000 sequencer, and converted to standard format, for example, using CASAVA pipeline, for example with custom scripts. In some implementations, after quality control, the 104 based reads are trimmed to 85 based per end for each paired end read. Data is aligned, for example, against hg18 (build 36) of human genome downloaded from UCSC genome browser and aligned using a custom pipeline consisting of, for example, BWA aligner, multiple scripts using genome analyses software packages including picard, GATK, and several custom scripts. In some implementations, variant calling is done using two callers: SAMtools (Li H., Handsaker B., Wysoker A., Fennell T., Ruan J., Homer N., Marth G., Abecasis G., Durbin R. and 1000 Genome Project Data Processing Subgroup (2009) The Sequence alignment/map (SAM) format and SAMtools. Bioinformatics, 25, 2078-9. [PMID: 19505943]) and VarScan (Genome Institute at Washington University). The called variants are compared with a list of known or putative variants, as would become apparent to a person of ordinary skill in the art.

EXAMPLE

Results

The following results, provided by way of example and not limitation, are related to flow sorting of tumor populations from archived FFPE samples.

Example 1

Previous studies have shown that DNA content based flow assays enable the discrimination of populations based on ploidy including, for example, diploid, aneuploid, polyploid and elevated $4N(G_2/M)$ fractions from fresh frozen biopsies of interest. These assays typically have coefficients of variation (c.v.) of +/−0.2N in the histograms for each population identified and can be combined with tissue and or tumor specific markers to sort subpopulations of diploid and aneuploid populations from routinely collected samples of interest. These sorted populations provided optimal templates for the high resolution detection of somatic aberrations in each cancer genome.

For example, homozygous deletions were meaningfully detected in aCGH experiments using objective thresholds (e.g., log$_2$ ratios <−3.0) even in samples with high admixtures (e.g., >90%) of non-tumor cells. FFPE material samples were initially de-waxed, rehydrated in sequential ethanol washes, treated with EDTA and then processed with a cocktail of enzymes, for example, collagenases and hyaluronidase to obtain single nuclei suspensions that were suitable for flow sorting. For each sample the nuclei were resuspended in DAPI NST, disaggregated with a 25-gauge needle, and then filtered through a 30-40-μm mesh filter immediately before analyses on an Influx cytometer, with ultraviolet excitation and DAPI emission collected at >450 nm. The flow rates were typically less than 1000 events/second and were adjusted accordingly for each sample based on sorting efficiency, the size and width of each peak of interest, and the presence of variable amounts of debris. DNA content and cell cycle were analyzed, as previously described, using the software program MultiCycle (Phoenix Flow Systems, San Diego, Calif.) 37. Multiple data were collected on the phenotype of each sample, including ploidy and cell cycle fractions ($G_0/G_1$, S, $G_2$/M) that were profiled in this study.

Figure 1:
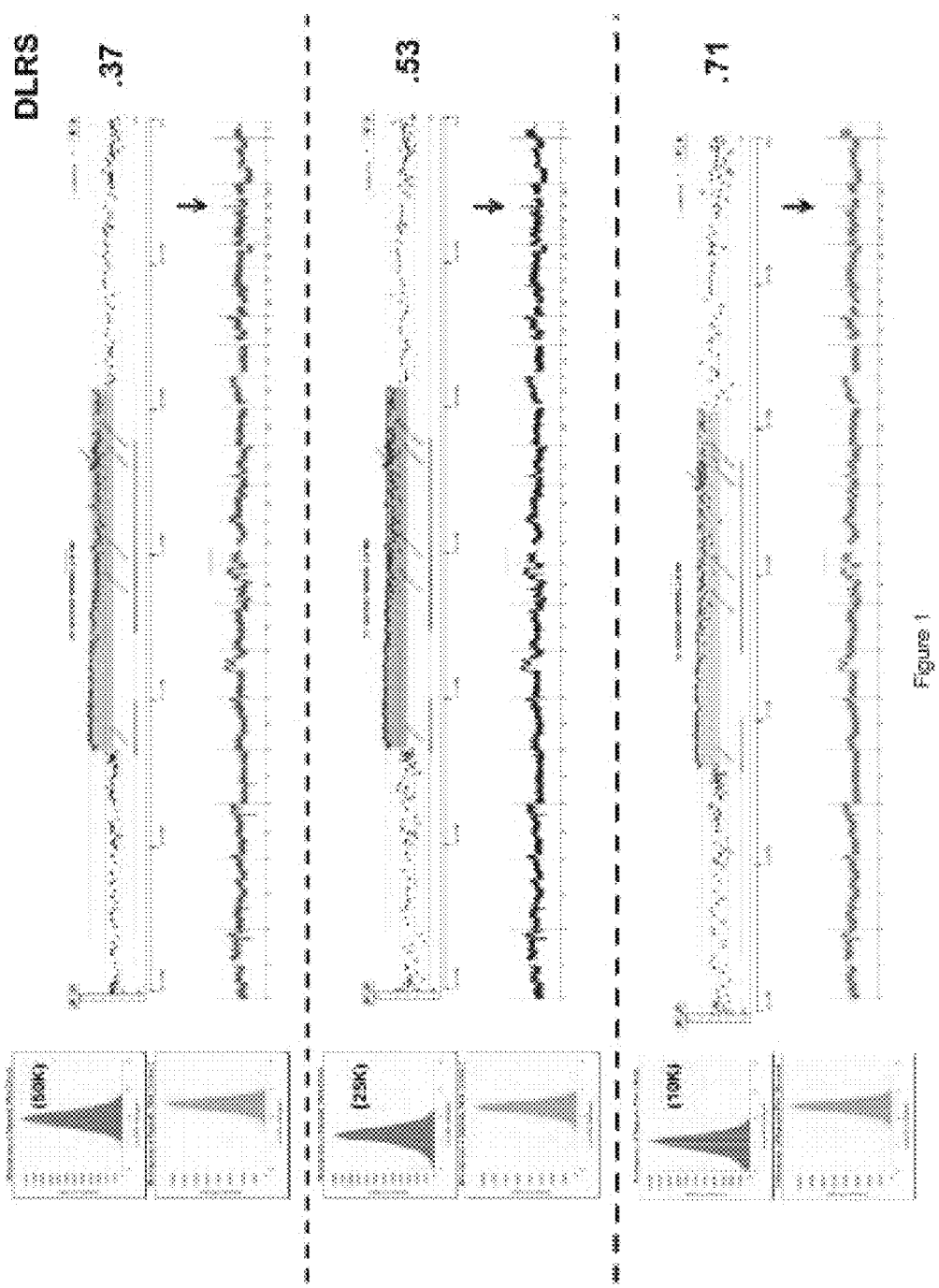
FIG. 1 depicts the effects of increasing inputs of DNA extracted from sorted nuclei from an FFPE breast cancer tissue sample. The signal intensities increased in a linear manner with increasing number of nuclei. The increased signal in the sample channel resulted in a corresponding decrease in the DLRS metric and improved resolution for aberration detection. Robust signals were obtained with an input of 50,000 sorted nuclei from the FFPE specimen.
Figure 15:
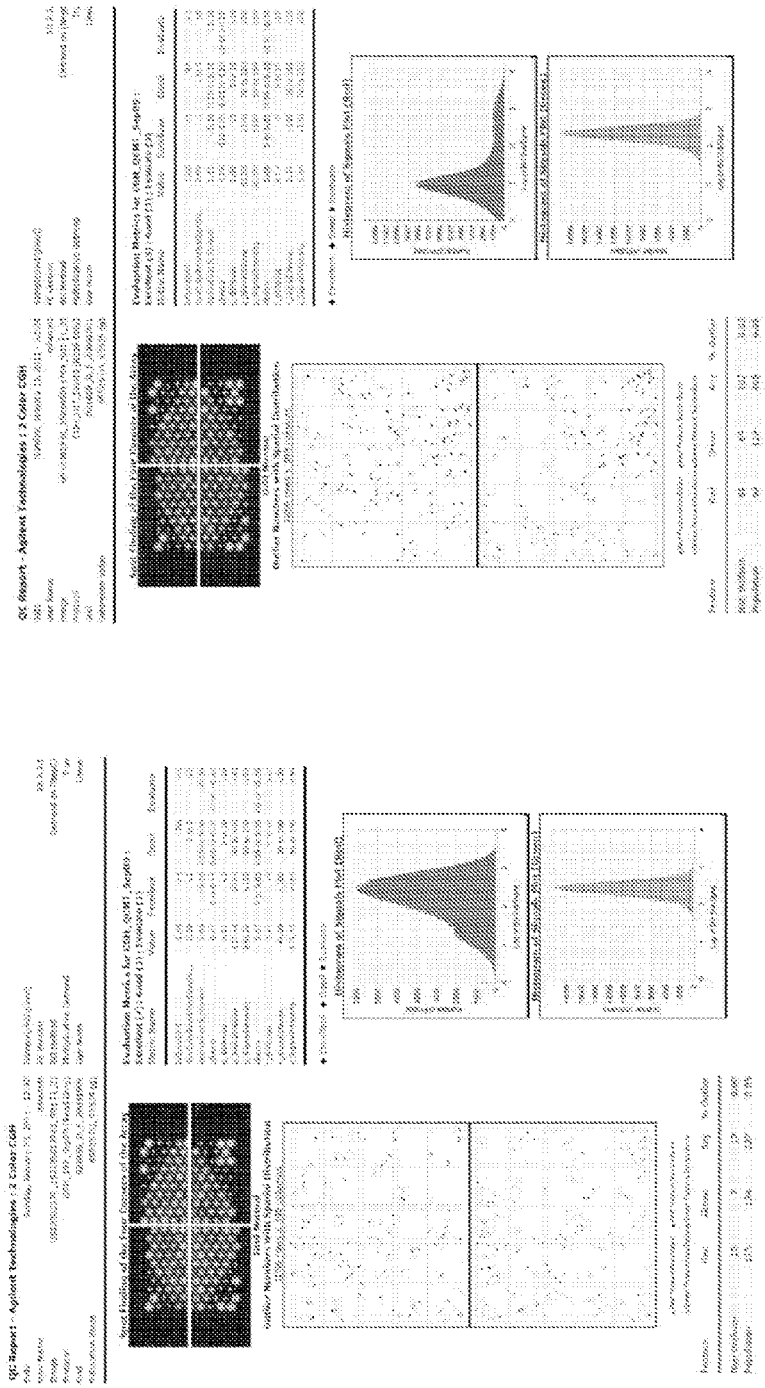
FIG. 15 shows the aCGH QC metrics for 2 sorted and amplified FFPE pancreatic cancer samples using 10,000 nuclei.
Figure 16:
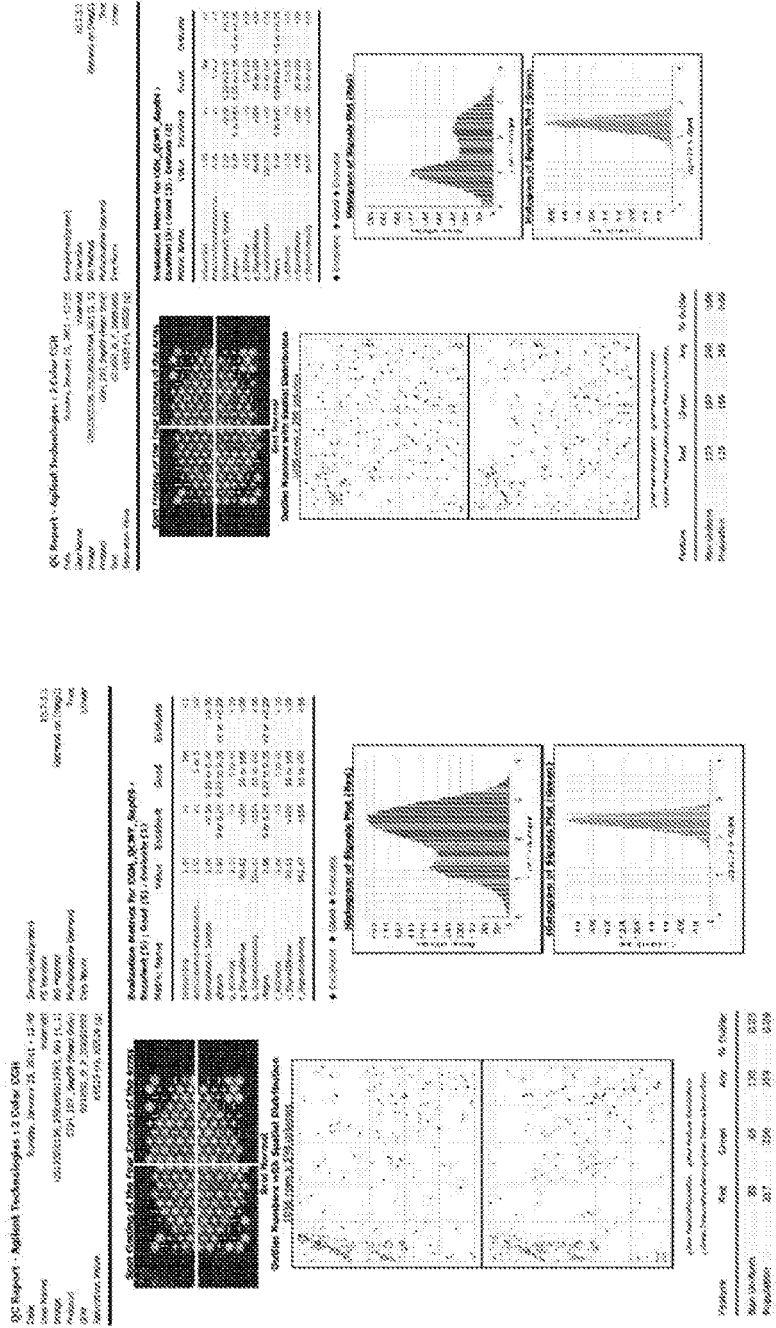
FIG. 16 shows the aCGH QC metrics for 2 sorted and amplified FFPE pancreatic cancer samples using 25,000 nuclei.
Figure 17:
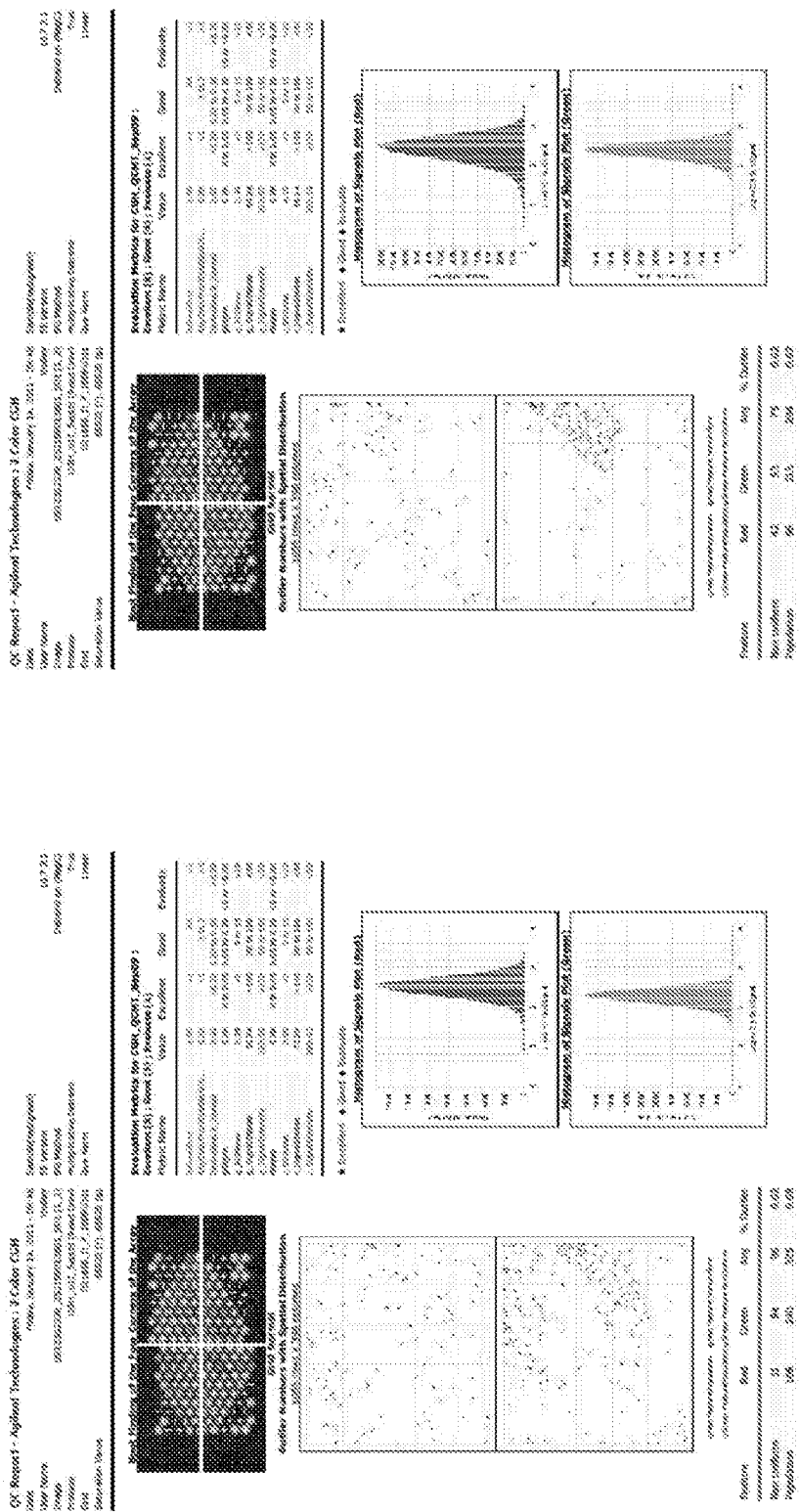
FIG. 17 shows the aCGH QC metrics for 2 sorted and amplified FFPE pancreatic cancer samples using 50,000 nuclei.

DNAs extracted from sorted FFPE fractions were then processed using optimized protocols for aCGH experiments using Agilent oligonucleotide arrays (See, e.g., FIGS. 15-17). Briefly, each DNA sample was digested to uniformity with DNAse 1 then labeled with Cy5 dye in Klenow labeling reactions. Initial experiments determined the number of sorted nuclei that were needed to provide robust aCGH results. Duplicate aliquots were sorted, having 10,000, 25,000, and 50,000 diploid and aneuploid (3.2N) nuclei from a single FFPE breast sample and the DNAs from each sorted sample processed for aCGH. All hybridizations were done with a pooled commercial 46,XX reference. To assess the utility of each sorted FFPE sample for aCGH analysis, a series of metrics were compared, as seen, for example, in FIG. 1, including background subtracted dye normalized signal intensities, the spread of the log ratios (DLRS) for each experiment, and the ability to map aberrant intervals in each genome.

Figure 2:
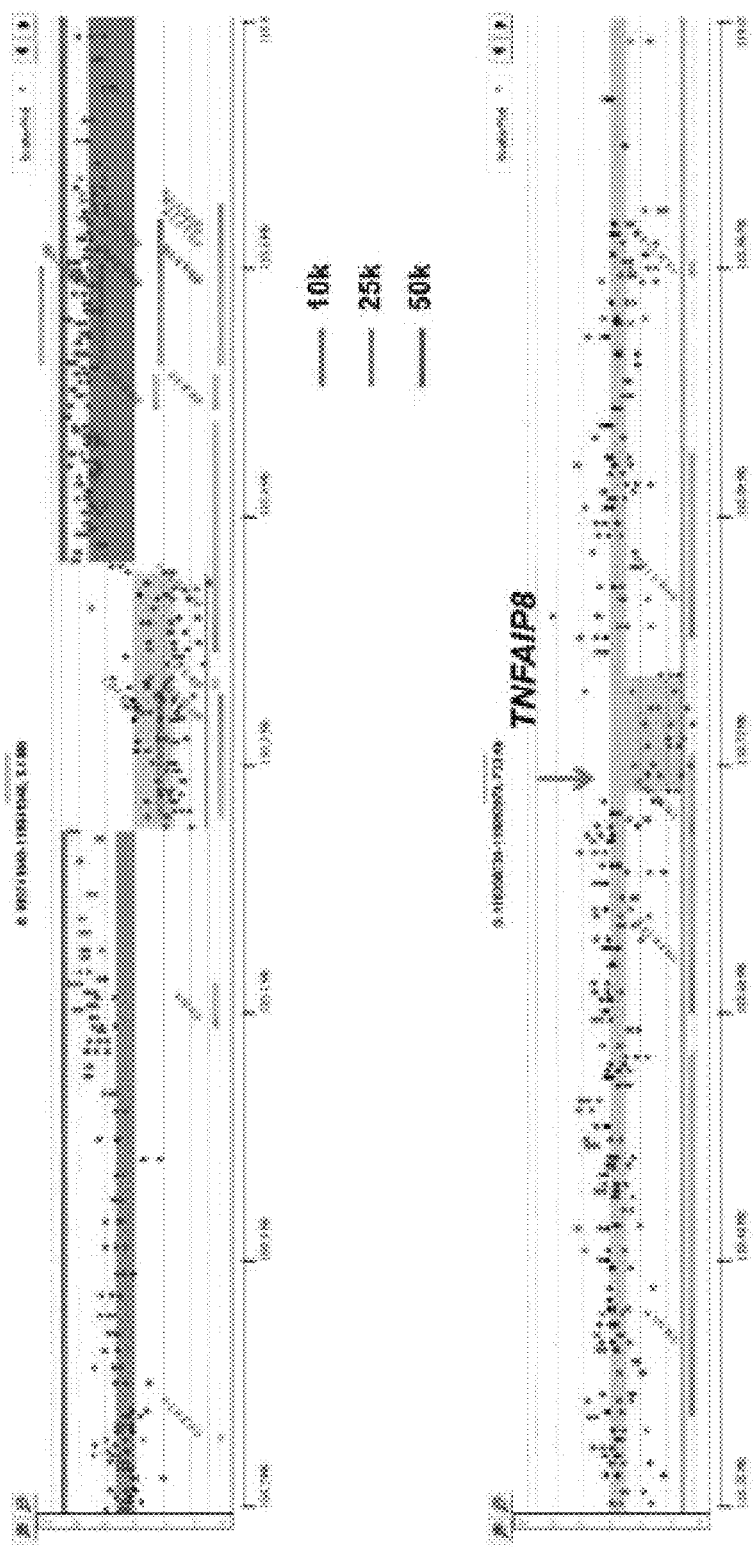
FIG. 2 shows a homozygous deletion ($\log_2$ ratio<-3) in tumor necrosis factor, alpha-induced protein 8 (TNFAIP8) a negative mediator of apoptosis was only detected in the 50 k sorted breast sample from FIG. 1.

The signal intensities of the sorted breast samples increased in a linear manner with increasing number of nuclei. Robust signals were obtained using 50,000 sorted nuclei from the FFPE specimen. The increased signal in the sample channel resulted in a corresponding decrease in the DLRS metric and improved resolution for aberration detection. For example, as seen in FIG. 2, although high level (log$_2$ ratio >1) amplicons were detected and mapped in all 3 samples, the weaker signals and broader distribution of ratios resulted in the progressive loss of detection for lower level amplicons, deletions, and the mapping of break points.

Significantly, a homozygous deletion (log$_2$ ratio <−3) in tumor necrosis factor, alpha-induced protein 8 (TNFAIP8) a negative mediator of apoptosis was only detected in the 50 k sample. Smaller volume arrays were used to increase the signal to noise levels in some implementations of the disclosed assays. An optimal level of signal to noise and probe coverage was obtained using the Agilent 400 k feature CGH arrays. The surface area of these arrays requires 400 μl volume hybridization compared to the 1 mL volume of the larger surface arrays (i.e., 244 k and 1000 k). Smaller surface arrays such as the 100 μL 4×180K array also gave increased signal to noise however these were limited by the lower coverage of the probes on the array and the need for shorter hybridization times (24 hours versus 40 hours) to avoid excess loss of hybridization solution during the recommended 65° C. hybridization.

Figure 3:
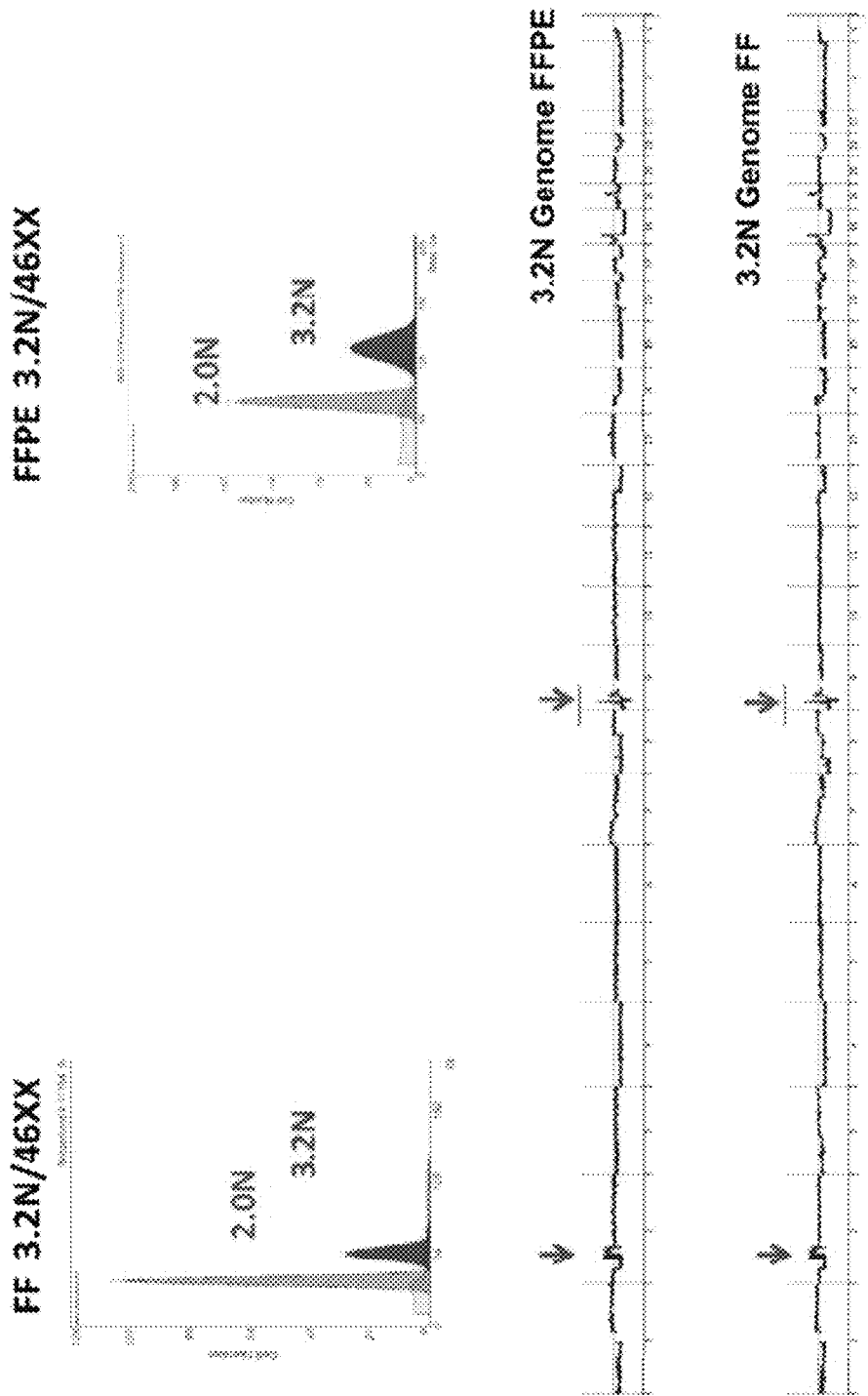
FIG. 3 shows a comparison of the flow sorts and aCGH for a matched FFPE and FF pancreatic cancer sample. The histograms show that the same 3.2N aneuploid tumor population was detected in each sample. The whole genome CGH plots show that the genomes of each sorted tumor sample were identical.

In order to further evaluate methods for sorting solid tissue FFPE samples, pancreatic ductal adenocarcinoma (PDA) samples were selected from tissues that had previously been characterized using fresh frozen material, flow sorting, and aCGH. A minimum of 50 k aneuploid nuclei were sorted from each of the samples. As seen, for example, in FIG. 3, the width of the histograms for the diploid and aneuploid (3.2N) peaks was greater for the FFPE sample likely reflecting the lower quality of the sample relative to the OCT embedded fresh frozen sample. The DNA from the sorted fresh frozen sample was amplified using phi29 methods prior to DNAse I digestion, labeling, and hybridization. In contrast, the low molecular weight DNA extracted from the FFPE nuclei was digested and labeled without amplification prior to hybridization.

Figure 4:
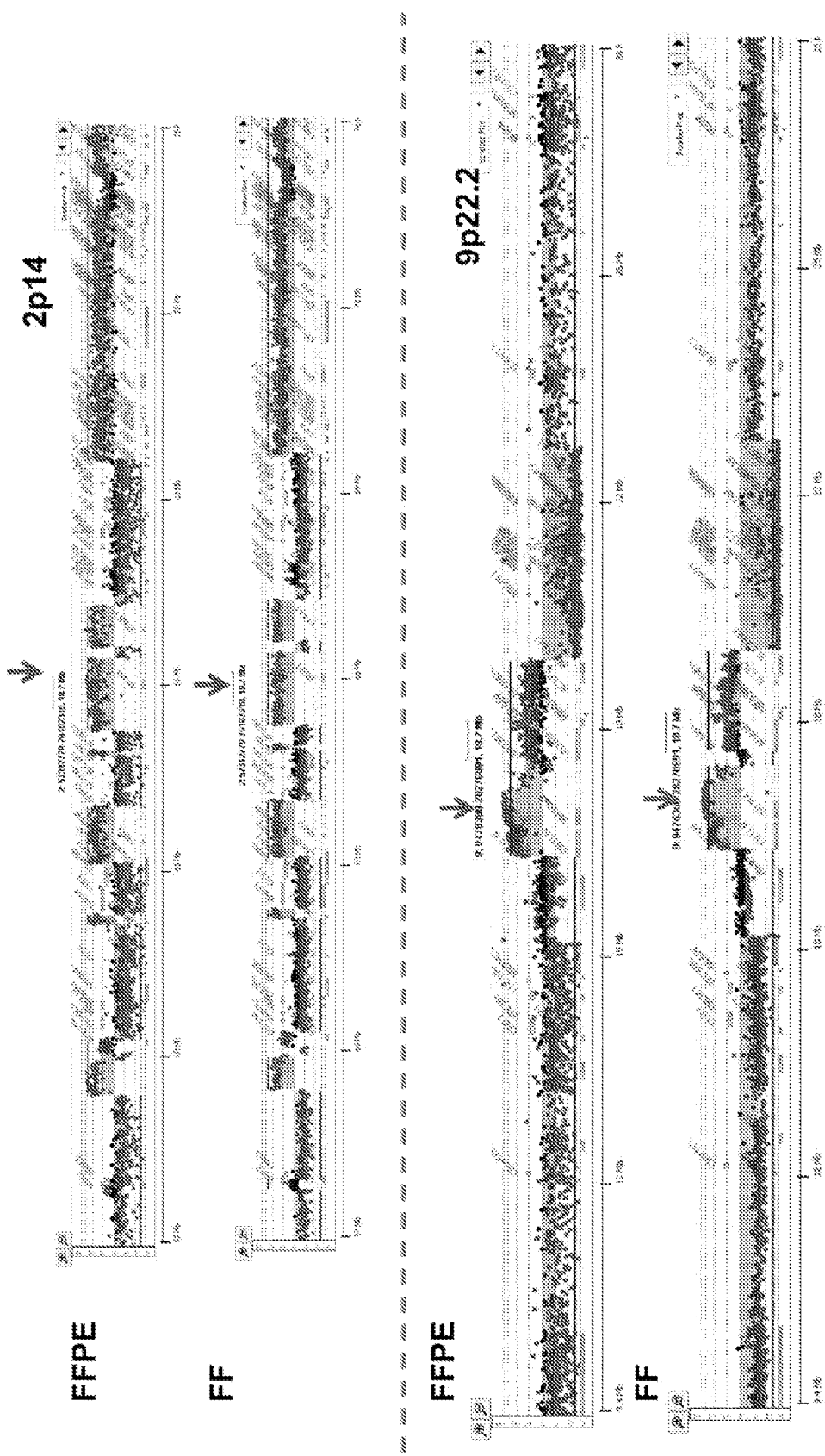
FIG. 4 shows specific examples (chromosome 2p14 and chromosome 9p22.2) of the overlap of intervals called by the ADM2 algorithm in the FFPE and FF sorted samples from FIG. 3.

After hybridization and feature extraction, a step gram algorithm (ADM2) was used to identify significant intervals in the CGH profiles of each sorted sample. The output from the ADM2 was used to measure the reproducibility of the aCGH data in matching FFPE and FF samples. Two aberrant intervals were called similar if their genomic regions overlapped by more than 0.5. The overlap of two intervals may be defined as the genomic length of their intersection divided by the genomic length of their union. The top twenty ranked amplicons in the FFPE sample were selected for this analysis. In 19 of these 20 amplicons, the overlap was >0.9 with the same ADM2 defined interval in the sorted fresh frozen sample. These intervals included a series of focal amplicons on chromosomes 2, 9, 18 and 19 (by way of example, some such intervals for chromosomes 2 and 9 are shown in FIG. 4) that targeted known and putative oncogenes.

These methods were then applied to a number of different tissues to assess the global utility of the FFPE assays disclosed herein. These samples included triple negative breast carcinomas, melanomas, glioblastoma, and small cell carcinoma of the ovary. These highly variable clinical samples were obtained from different tumor banks. In each case aberrations in the sorted samples were discriminated to the same resolution as with fresh frozen samples. Each had highly variable genomes with different levels of instability and number and extent of aberrations. These included clinically important aberrations including highly focal amplicons in EGFR, and homozygous deletions in JMJD1C, CDKN2A, and PTEN.

Example 2

Next Generation Sequencing (NGS)

According to embodiments, next generation sequencing, including parallel sequencing, is used to ascertain the exome and/or genome sequences. The following is provided as an example implementation where next generation sequencing is used.

Current methods of NGS typically require larger amounts of DNA template as input. Furthermore widely used methods are dependent on genomic DNA templates of highly uniform quality as inputs for efficient library construction. For fresh frozen samples, the use of phi29 can generate high molecular weight template for aCGH experiments. This linear amplification method is dependent on intact templates, such as, samples from high quality fresh frozen biopsies. However, the small fragment sizes of DNAs typically isolated from routine FFPE samples are not suited for linear amplification with highly processive enzymes such as phi29.

The use of the single primer isothermal amplification (SPIA) was investigated to generate templates from sorted FFPE samples that are suitable for both aCGH and next generation sequencing. To test this method, the comparisons of the aCGH data with matching FF, non amplified FFPE, and SPIA FFPE samples were repeated. The minimum input was determined for the SPIA reaction to give template that could be used in aCGH experiments. Aliquots of 10,000, 25,000 and 50,000 nuclei were collected during sorts of individual pancreas FFPE samples. Each sorted aliquot was extracted, labeled, and then hybridized to 400 k CGH arrays.

Figure 5:
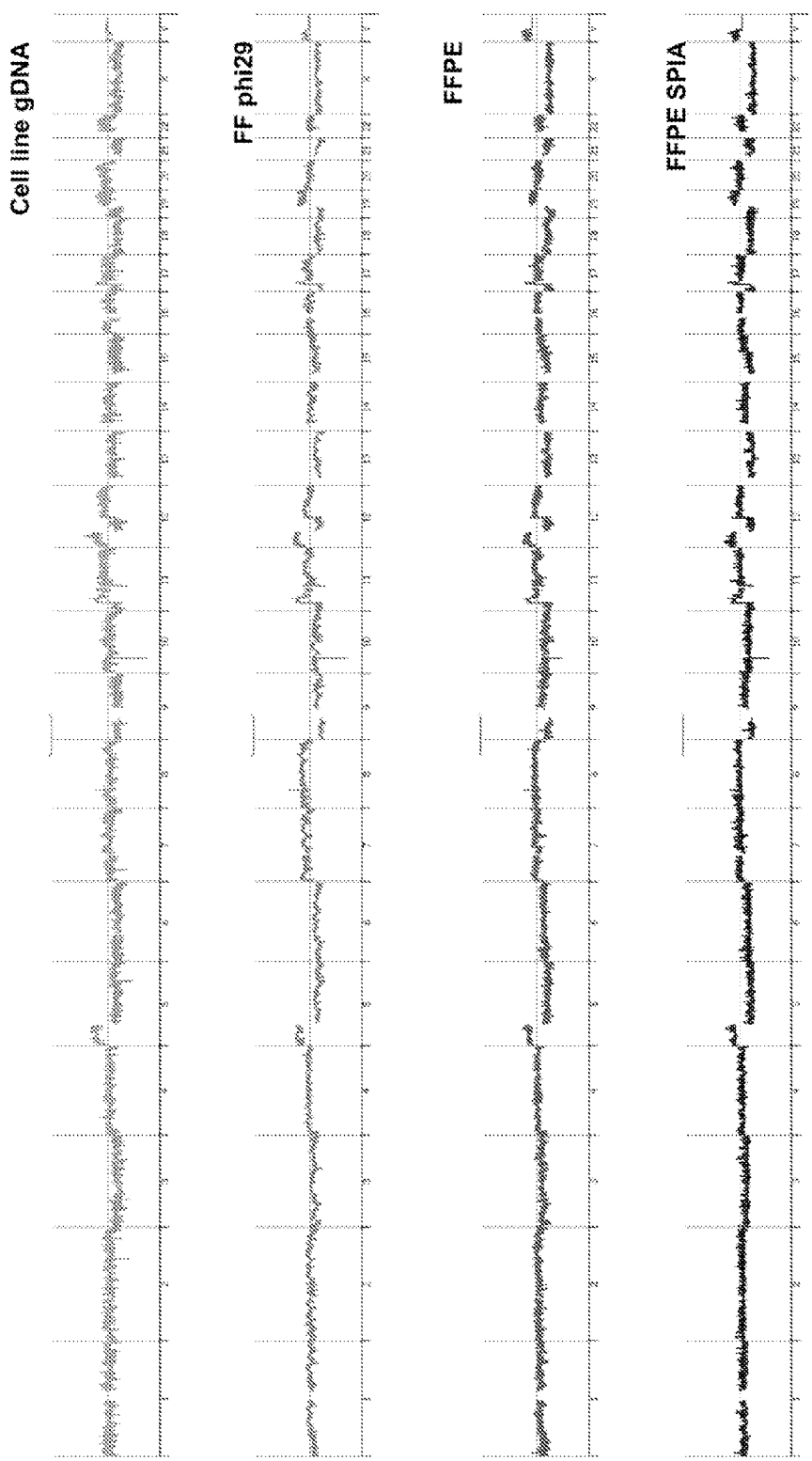
FIG. 5 shows the overlap for the aCGH profiles of the cell line, sorted FF amplified, sorted FFPE, and sorted FFPE amplified A10 samples that were derived from the same patient tissue sample.
Figure 7:
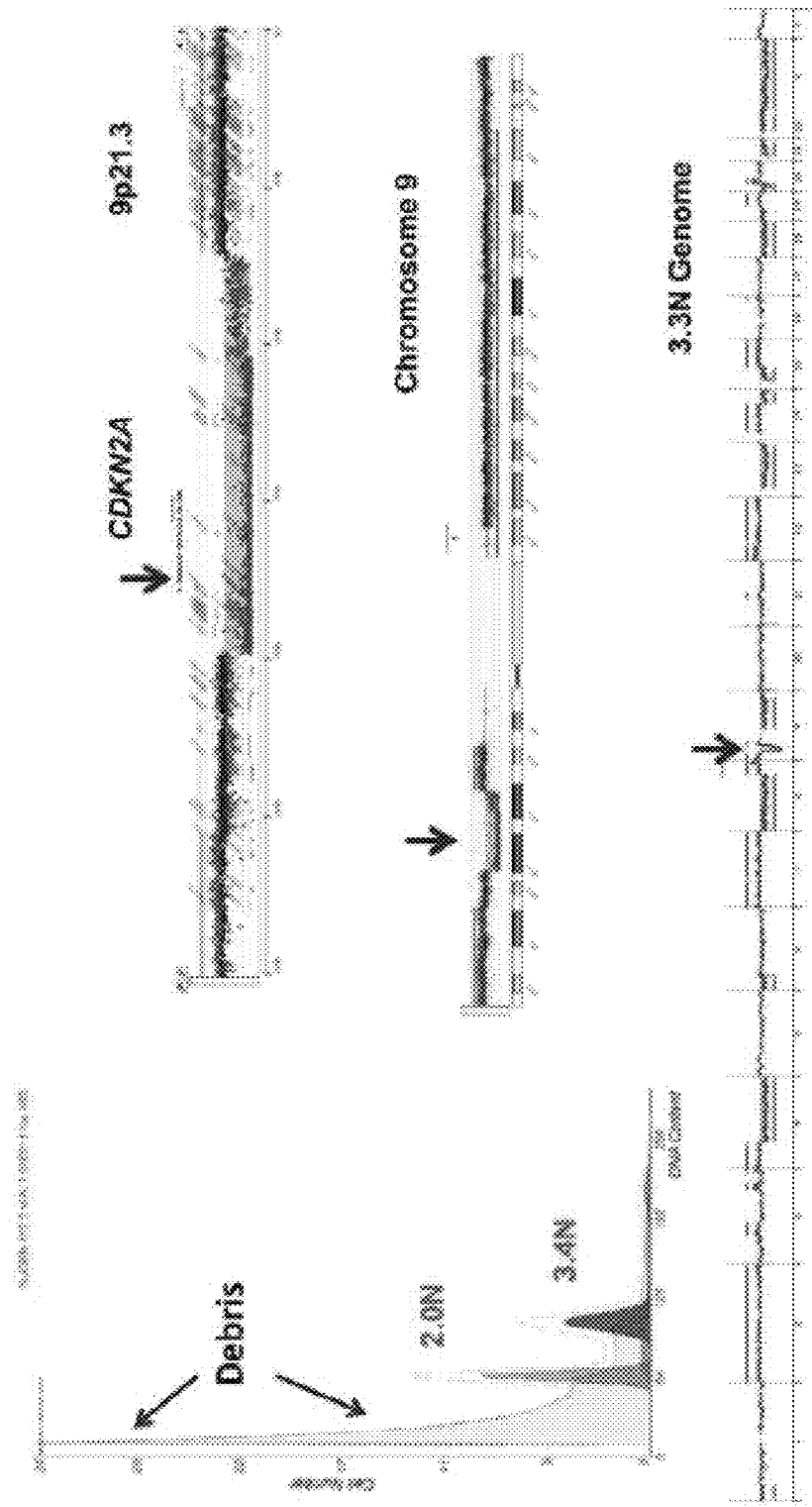
FIG. 7 shows an example of whole genome CGH analysis of flow sorted FFPE PDA sample: A) histogram of diploid (2.0N) and aneuploid (3.4N) cells sorted from metastatic PDA FFPE sample, and B-D) whole genome, chromosome 9, and 9p21 CGH plots demonstrating homozygous deletion of CDKN2A gene in 3.4N tumor population. Blue shaded areas denote copy number aberrant regions called by ADM2 step gram algorithm.
Figure 9:
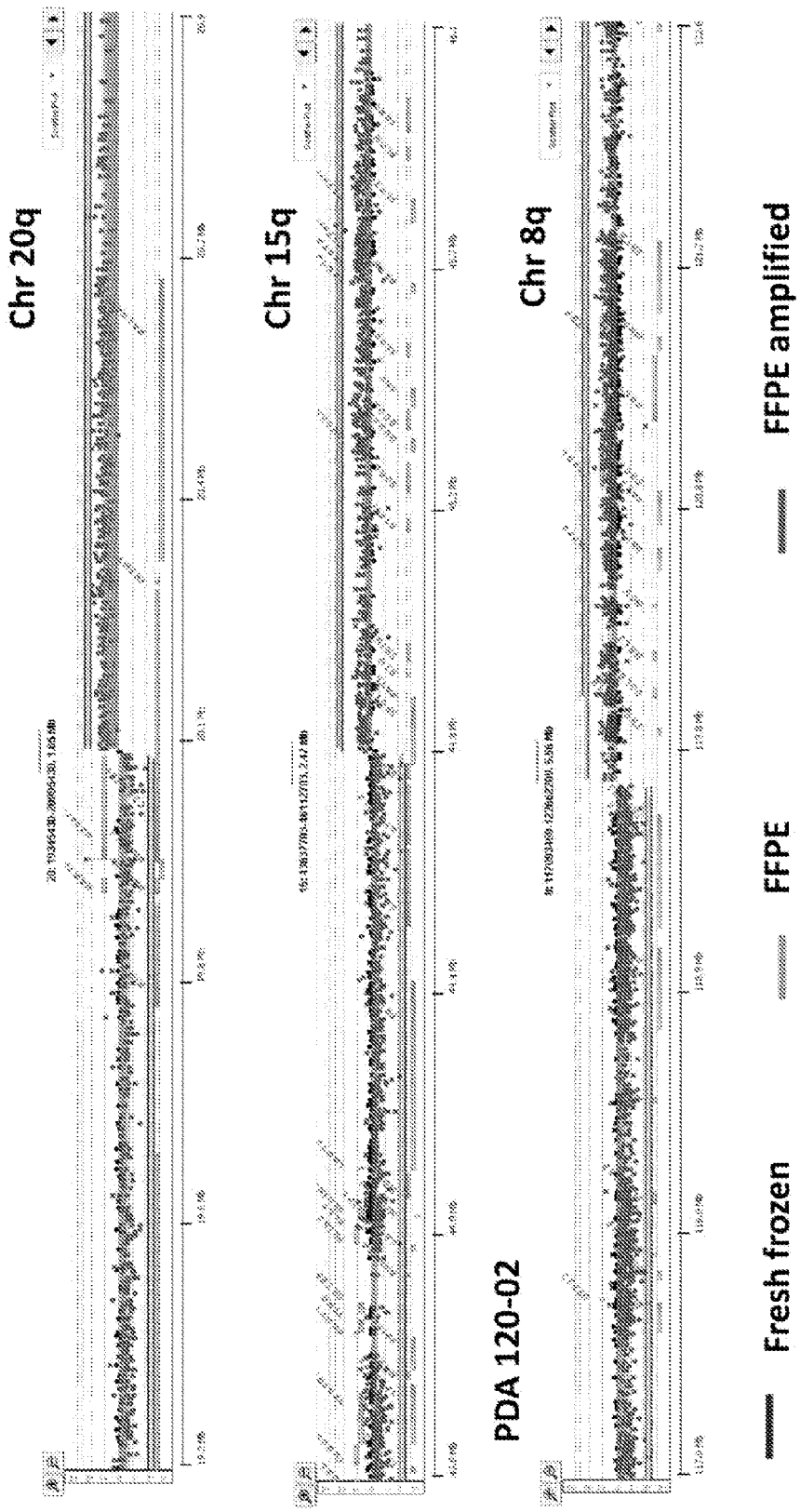
FIG. 9 shows examples of overlap in the ADM2 defined intervals in aCGH profiles and their associated breakpoints in FF, FFPE, and FFPE amplified sorted PDA sample.
Figure 11:
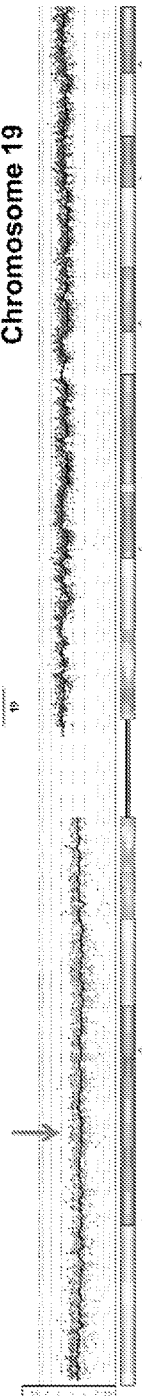
FIG. 11 shows the detection of a homozygous mutation in SMARC4 in the cell line, sorted FF and sorted FFPE PDA samples from the same tissue and the corresponding CGH plot of chromosome 19 with copy number loss at 19p.

In each case, the amplified product labeled to high specificity as assessed by the specific activity of each sample. As shown, for example, in FIG. 5, the 50,000 nuclei samples gave robust signals on the array as measured by the histogram of the dye normalized background subtracted signals in the sample (Cy 5) channel. In contrast, there was a second non-specific peak in the array data obtained with the lower input samples. This suggests that non-specific products were present in the amplification reaction that although they labeled efficiently did not hybridize to the unique human sequences of the CGH probes. These also correlated with the distribution of the $\log_2$ ratios from the array data and the ability to detect the aberrant genomic intervals in each genome. In each case the same intervals were detected in each of the samples. These data show that at least 10,000, more preferably at least 25,000, and most preferably 50,000, nuclei input provides sufficient template for the linear whole genome amplification of tumor samples.

To assess the utility of SPIA amplified sorted FFPE samples for NGS 50,000 nuclei were resorted from a FFPE PDA sample (JHU A10-AT) for which there was also a matching fresh frozen sorted sample (JHU A10-46), as well as a cell line (JHU A10-74) derived from the same tissue. The SPIA amplification was repeated with 50,000 FFPE nuclei input. Template was prepared for sequencing by amplifying 100 ng of genomic DNA from the sorted fresh frozen sample with a phi29 protocol, and from unamplified genomic DNA extracted from the cell line. The CGH profile of each of these three samples was identical as assessed by the presence of ADM2 determined intervals and the ploidy of the tumor cells. In addition, the exome of the cell line has been previously reported. A 3 ug aliquot of SPIA amplified FFPE, phi 29 amplified FF, and cell line genomic DNA were then used as input for exome sampling and whole genome library preparations.

A comparison of the unique paired end reads in each of the 3 samples showed that at a 20× coverage almost 80% of the reads mapped to concordant unique regions of the genome. This is demonstrated, as an example, in FIG. 6. The previously reported 34 non-synonymous mutations were compared across the 3 samples. In ten cases there was no call made by the variant caller. These all mapped to regions that were not covered by capture oligonucleotides in the Agilent Sure Select reagents. Strikingly, the remaining 24 mutations were all detected in each sample preparation. In each case the heterozygous or homozygous state of the mutation was consistent across each sample preparation.

Example 3

Aberration Detection and aCGH of Flow Sorted Populations from Breast Carcinoma, Bladder Carcinoma, Glioblastoma, and Ovarian Carcinoma To assess the universal utility of the FFPE assays with different tissues samples, TNBC, bladder carcinoma, glioblastoma, and small cell carcinoma of the ovary (SCCO) were analyzed (FIGS. 19-23) and selected aberrations were verified by (fluorescence in situ hybridization) FISH (FIG. 24). Fluorescence in situ hybridizations (FISH) were performed as previously described by Ruiz, et al. (2011) *Proc Natl Acad Sci USA* 108:12054. Hybridization and post-hybridization washes were done according to the 'LSI procedure' (Vysis, Abbott Park, Ill.). Hybridizations with the 9p21 (ZytoLight SPEC p16/CEN9 Dual probe, Zytovision) and the Cyclin D1 (ZytoLight SPEC CCND1/CEN11 Dual probe, Zytovision) FISH probes were performed overnight in a humidified chamber at 37° C. All FISH analyses were independently evaluated by two people. Images were obtained by use of an Axioskop 40 fluorescence microscope (Zeiss, Oberkochen, Germany) equipped with a 63× objective and an Axiocam MRm camera (Zeiss).

The tumor samples were obtained from multiple tumor banks and contained variable amounts of debris and non-tumor cells. Single parameter DNA content assays were used to detect and sort the diploid, aneuploid, and 4N cell populations present in each sample. In each case, homozygous and partial deletions were discriminated, and map breakpoints and amplicon boundaries were identified to the single gene level in the sorted samples regardless of tumor cell content. These included potentially clinically relevant aberrations such as focal amplicons of EGFR, USP25, and CCND1, and homozygous deletions in PARD3, CDKN2A, and PTEN. These latter aberrations included single exon deletions. One striking exception was SCCO, a rare tumor that presents in young women and girls. The SCCO genomes did not contain any focal amplicons or homozygous deletions. However, the resolution of the assays with FFPE samples allowed the mapping of a 1p36.22 breakpoint created by a single copy loss to the CASZ1 locus, a zinc finger gene implicated in neuroblastoma (FIG. 23).

Example 4

Clonal Evolution Underlying Transplacental Transfer and Vemurafenib Resistance in Melanoma Intratumor heterogeneity can lead to underestimation of the tumor genomics landscape portrayed from single tumor-biopsy samples and may present major challenges to personalized-medicine and biomarker development (Ruiz, C, et al. (2011) *PNAS* 108:12054). Intratumor heterogeneity, associated with heterogeneous protein function, may foster tumor adaptation and therapeutic failure through Darwinian selection (Gerlinger et al. (2012) *N Engl J Med* 366:883). This is further illustrated in the analysis of melanoma diagnosed in a mother and her infant that follows.

The emerging evidence suggests cancer is a dynamic and diverse evolutionary ecosystem, composed of coexisting, molecularly distinct subpopulations of cells that may have distinct molecular and biological characteristics. To evaluate this issue, the assays of the present invention were used to study tumor heterogeneity in solid tumors, specifically melanoma, based on separation of cellular subpopulations using nuclear flow sorting coupled to high-definition genomic analyses, i.e., array-based comparative genomic hybridization and next generation sequencing.

This approach was applied to study an unusual case of transplacentally-transferred melanoma. The mother developed a BRAF V600E positive metastatic melanoma during her pregnancy, and vemurafenib treatment was initiated after delivery. Within weeks of delivery the infant developed multiple cutaneous lesions consistent with BRAF V600E positive metastatic melanoma and was initiated on a modified vemurafenib protocol. The clinical history of the mother and infant is summarized below (see also FIG. 25).

- 26-year-old, white, female Subject diagnosed with primary melanoma on the left face (location, AJCC). Subject underwent wide local excision.
- Subject delivered a healthy infant girl (Infant Subject) by Caesarean section.
- The Subject experienced a tonic-clonic seizure—multiple metastases (mets) in central nervous system (CNS), lung, and bone; identified as squamous cells (SQ). A lung needle biopsy confirmed melanoma.
- Whole Brain Radiation Therapy (WBRT) was complicated by brain hemorrhage.
- Craniotomy and resection of the metastatic brain lesion.
- Initiated temozolomide (TMZ) therapy.
- Identified BRAF V600E mutation.
- Progressive disease on the first cycle of TMZ (imaging).
- Parents became concerned about two dark spots on the scalp of Infant Subject at 3-months of age.
- Subject started vemurafenib at 800 mg PO BID.
- Positron emission tomography-computed tomography (PET CT) scans from Subject compared and indicated resolution of multiple lung nodules, reduction in multiple systemic tumors in lymph nodes as well as subcutaneous tissues and a reduction in SUV in nearly all lesions.
- Subject experienced dysarthria—brain MRI—increase in the size of three pre-existing CNS metastases and a new metastatic deposit of a 1.1 cm lesion in the left frontal lobe.
- Subject underwent stereotactic radiosurgery (STRS) to the new metastatic lesion. Subject's functional status dramatically improved and her pain had significantly resolved to the point that she was maintained on low doses of narcotic analgesics.
- Subject experienced increasing radicular low back pain—progressing metastatic disease in the L5-S1 region and she was begun on STRS.
- PET CT scan confirmed systemic relapse with new scalp as well as innumerable lesions in the soft tissues, nodal regions and lungs. Previously noted liver metastasis was no longer identified. The Subject deteriorated rapidly and was no longer a candidate for systemic therapy.
- Biopsy of a progressing left shoulder mass performed.
- Subject died.

Tissues available for analysis from the mother included FFPE samples of lung and brain, a frozen biopsy from the shoulder, and a buccal swab while those from the infant included two separate FFPE samples from the scalp (see FIG. 26). The complexity of these samples makes tumor profiling difficult if not impossible without nuclear flow cytometry (see FIG. 27). By using the methods of the present disclosure, it was possible to separate sub-populations from the samples and identify genomic aberrations. This process is outlined in FIGS. 28-30.

Both the mother and the infant demonstrated initial response to vemurafenib. While the mother quickly relapsed and rapidly progressed, the infant continued to respond to vemurafenib. Clonal analysis of melanoma tissues from the mother (pre-vemurafenib and at progression) and the infant (pre-vemurafenib) indicates that the mother harbored at least two related but distinct clones, only one of which was identified in the infant (see FIGS. 31-37). Vemurafenib treatment suppressed the shared clone in both mother and infant, while the second, unique clone progressed in the mother and led to relapse (see FIGS. 38-39). The second unique clone was found to contain a mutation in the c-jun gene, which maps to the 1p32-p31 chromosomal region (see FIG. 39). This chromosomal region is involved in both translocations and deletions in human malignancies.

These data illustrate the role of clonal heterogeneity in mediating key clinical events related to tumor progression, response to therapy, and development of resistance; a major challenge of targeted BRAF therapies. The data also highlight the potential of the disclosed methods to guide therapeutic interventions in cancer patients.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application, which are each herein incorporated by reference for all purposes, including, Holley, T. et al. (2012), "Deep clonal profiling of formalin fixed paraffin embedded clinical samples" *PLOS ONE* Vol. 7. Issue 11, e50586. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of identifying aberrations in a variable cancer cell genome sample, comprising:
    obtaining a cancerous tumor sample comprising normal and abnormal cells;
    creating a suspension of de-agglomerated nuclei of the cells suitable for flow sorting;
    sorting the nuclei into a plurality of fractions based at least on a quantification of genetic material in the nuclei;
    extracting the genetic material from at least a portion of the sorted nuclei;
    differentially labeling the extracted genetic material and a reference sample;
    hybridizing the labeled extracted genetic material and reference sample on a feature comparative genomic hybridization array;
    comparing the labeled extracted genetic material with the labeled reference sample to infer aberrations unique to the labeled extracted genetic material;
    preparing a fragmented library comprising a whole genome library and/or an exome library from the extracted genetic material;
    amplifying the fragmented library by generating a plurality of paired-end clusters from a plurality of fragments from the fragmented library; and,
    determining the sequence of the plurality of fragments through parallel sequencing;

wherein an aberration interval in the extracted genetic material is considered similar to an aberration interval in the labeled reference sample when an overlap exceeds about 0.5, wherein the overlap of two aberration intervals comprises the genomic length of their intersection divided by the genomic length of their union.

2. The method of claim 1, wherein the cancerous tumor sample comprises a formalin fixed paraffin embedded (FFPE) cancerous tumor sample.

3. The method of claim 1, wherein the aberrations are detected in the course of a single-patient diagnosis and with the use of an aberration detection algorithm; or the portion of the sorted nuclei from which the genetic material is extracted comprises at least two fractions.

4. The method of claim 3, further comprising inferring genomic tumor evolution based on a comparison between aberrations in the genetic material from the plurality of fractions and treatment history of the patient.

5. The method of claim 1, wherein the cancerous tumor is selected from the group consisting of: breast cancer, large intestinal cancer, lung cancer, small lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, vaginal carcinoma, Hodgkin's disease, non-Hodgkin's lymphoma, esophageal cancer, small intestine cancer, endocrine cancer, thyroid cancer, parathyroid cancer, adrenal cancer, chronic or acute leukemia, soft tissue tumor, urethral cancer, penile cancer, prostate cancer, lymphocytic lymphoma, bladder carcinoma, kidney cancer, ureter cancer, renal carcinoma, renal pelvic carcinoma, CNS tumor, primary CNS lymphoma, bone marrow tumor, brain stem nerve gliomas, pituitary adenoma, testicular cancer, oral cancer, pharyngeal cancer and uveal melanoma.

6. The method of claim 5, wherein the cancerous tumor is selected from the group consisting of a prostate adenocarcinoma, a pancreatic adenocarcinoma, a breast carcinoma, a bladder carcinoma, a glioblastoma, an ovarian carcinoma, and a melanoma.

7. The method of claim 1, wherein sorting the nuclei further comprises using a flow cytometer.

8. The method of claim 7, wherein using a flow cytometer comprises using a flow rate of between about 50 and about 1500 events per second; between about 100 and about 1000 events per second; or between about 300 and about 700 events per second.

9. The method of claim 7, wherein using a flow cytometer comprises using a flow stream differential pressure (sheath/sample) of between about 0.1 and about 1.0; between about 0.4 and about 1.0; or between about 0.6 and about 1.0.

10. The method of claim 7, further comprising achieving an acceptable sorting efficiency of at least about 60%; at least about 70%; or at least about 80%.

11. A method of identifying aberrations in a variable cancer cell genome derived from a formalin fixed paraffin embedded (FFPE) cancerous tumor sample, comprising:
dewaxing the sample;
rehydrating the sample;
treating the sample to obtain a suspension of de-agglomerated nuclei suitable for flow sorting;
sorting the nuclei into a plurality of fractions based at least on a quantification of genetic material in the nuclei;
profiling the ploidy and cell cycle fractions of the nuclei;
extracting the genetic material from at least a portion of the sorted nuclei;
amplifying the genetic material through single primer isothermal amplification; and,
digesting the genetic material to substantial uniformity with an endonuclease;
differentially labeling the digested genetic material and a reference sample;
hybridizing the labeled digested genetic material and reference sample on a feature comparative genomic hybridization array;
comparing, with an aberration detection algorithm, the labeled digested genetic material with the labeled reference sample to infer aberrations unique to the labeled digested genetic material;
preparing from the digested genetic material a fragmented library comprising a whole genome library or an exome library from the extracted genetic material;
amplifying the fragmented library by generating a plurality of paired-end clusters from a plurality of fragments from the fragmented library; and
determining the sequence of the plurality of fragments through parallel sequencing;
wherein an aberration interval in the extracted genetic material is considered similar to an aberration interval in the labeled reference sample when an overlap exceeds about 0.5, wherein the overlap of two aberration intervals comprises the genomic length of their intersection divided by the genomic length of their union.

12. The method of claim 11, wherein treating the sample comprises processing the sample with EDTA, collagenase, and hyaluronidase.

13. The method of claim 11, wherein the number of sorted nuclei is at least 50,000.

14. The method of claim 11, further comprising, prior to sorting the nuclei, staining the nuclei with 4',6-diamidino-2-phenylindole and/or wherein the endonuclease is DNAse 1.

15. The method of claim 11, wherein the cancerous tumor is selected from the group consisting of: breast cancer, large intestinal cancer, lung cancer, small lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, vaginal carcinoma, Hodgkin's disease, non-Hodgkin's lymphoma, esophageal cancer, small intestine cancer, endocrine cancer, thyroid cancer, parathyroid cancer, adrenal cancer, chronic or acute leukemia, soft tissue tumor, urethral cancer, penile cancer, prostate cancer, lymphocytic lymphoma, bladder carcinoma, kidney cancer, ureter cancer, renal carcinoma, renal pelvic carcinoma, CNS tumor, primary CNS lymphoma, bone marrow tumor, brain stem nerve gliomas, pituitary adenoma, testicular cancer, oral cancer, pharyngeal cancer and uveal melanoma.

16. The method of claim 15, wherein the cancerous tumor is selected from a group consisting of a prostate adenocarcinoma, a pancreatic adenocarcinoma, a breast carcinoma, a bladder carcinoma, a glioblastoma, an ovarian carcinoma, and a melanoma.

17. The method of claim 11, wherein the reference sample is a pooled 46, XX reference sample.

18. The method of claim 11, wherein the array requires a hybridization volume of at least 400 microliters.

* * * * *